United States Patent
Sawchuk

(10) Patent No.: US 10,286,221 B2
(45) Date of Patent: May 14, 2019

(54) OPERATION OF AN EXTRACARDIOVASCULAR IMPLANTABLE CARDIOVERTER DEFIBRILLATOR (ICD) DURING IMPLANTATION OF ANOTHER MEDICAL DEVICE

(71) Applicant: Medtronic, Inc., Minneapolis, MN (US)

(72) Inventor: Robert T. Sawchuk, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 158 days.

(21) Appl. No.: 15/143,114

(22) Filed: Apr. 29, 2016

(65) Prior Publication Data

US 2017/0312531 A1    Nov. 2, 2017

(51) Int. Cl.
*A61N 1/39*     (2006.01)
*A61N 1/362*    (2006.01)
*A61N 1/372*    (2006.01)
*A61N 1/375*    (2006.01)
*A61N 1/08*     (2006.01)
(Continued)

(52) U.S. Cl.
CPC .............. *A61N 1/3962* (2013.01); *A61N 1/08* (2013.01); *A61N 1/3621* (2013.01); *A61N 1/3756* (2013.01); *A61N 1/37241* (2013.01); *A61N 1/37264* (2013.01); *A61N 1/37288* (2013.01); *A61N 1/3987* (2013.01); *A61N 1/025* (2013.01); *A61N 1/0563* (2013.01); *A61N 1/39622* (2017.08)

(58) Field of Classification Search
CPC .............. A61N 1/37264; A61N 1/3962; A61N 1/3621; A61N 1/3987; A61N 1/37288; A61N 1/3756
See application file for complete search history.

(56) References Cited

U.S. PATENT DOCUMENTS

| | | |
|---|---|---|
| 4,494,950 A | 1/1985 | Fischell |
| 5,117,824 A | 6/1992 | Keimel et al. |
| 5,354,316 A | 10/1994 | Keimel |

(Continued)

FOREIGN PATENT DOCUMENTS

WO    2015164167 A1    10/2015

OTHER PUBLICATIONS

Demmer, "Multi-Device Implantable Medical Device System and Programming Methods", U.S. Appl. No. 14/601,915, filed Jan. 21, 2015, 71 pages.

(Continued)

*Primary Examiner* — William J Levicky

(57) ABSTRACT

Techniques are disclosed for determining, by an extracardiovascular implantable cardioverter defibrillator (ICD) implanted in a patient, whether one or more test therapy signals generated by another medical device implanted in the patient is detected. In response to detecting the one or more test therapy signals, the extracardiovascular ICD provides an indication that the extracardiovascular ICD has detected the one or more test therapy signals. In some examples, the indication is an audible tone provided to a clinician. In some examples, the other medical device is an intracardiac cardiac pacing device, and the one or more test therapy signals comprises a plurality of anti-tachycardia pacing (ATP) pulses.

27 Claims, 12 Drawing Sheets

(51) Int. Cl.
*A61N 1/02* (2006.01)
*A61N 1/05* (2006.01)

(56) References Cited

U.S. PATENT DOCUMENTS

| | | | |
|---|---|---|---|
| 5,456,692 A | 10/1995 | Smith, Jr. et al. | |
| 5,507,782 A | 4/1996 | Kieval et al. | |
| 5,545,186 A | 8/1996 | Olson et al. | |
| 5,683,432 A | 11/1997 | Goedeke et al. | |
| 5,725,559 A | 3/1998 | Alt et al. | |
| 5,755,736 A | 5/1998 | Gillberg et al. | |
| 6,272,379 B1 * | 8/2001 | Fischell | A61N 1/3925 600/515 |
| 6,393,316 B1 | 5/2002 | Gilberg et al. | |
| 6,442,433 B1 | 8/2002 | Linberg | |
| 6,471,645 B2 | 10/2002 | Warkentin et al. | |
| 6,599,250 B2 | 7/2003 | Webb et al. | |
| 6,647,434 B1 | 11/2003 | Kamepalli | |
| 6,892,094 B2 | 5/2005 | Ousdigian et al. | |
| 7,031,771 B2 | 4/2006 | Brown et al. | |
| 7,181,505 B2 | 2/2007 | Haller et al. | |
| 7,565,197 B2 | 7/2009 | Haubrich et al. | |
| 7,610,092 B2 | 10/2009 | Cowan et al. | |
| 7,720,543 B2 | 5/2010 | Dudding et al. | |
| 7,742,816 B2 | 6/2010 | Masoud et al. | |
| 7,949,404 B2 | 5/2011 | Hill | |
| 8,102,789 B2 | 1/2012 | Rosar et al. | |
| 8,160,684 B2 | 4/2012 | Ghanem et al. | |
| 8,352,025 B2 | 1/2013 | Jacobson | |
| 8,352,038 B2 | 1/2013 | Mao et al. | |
| 8,433,409 B2 | 4/2013 | Johnson et al. | |
| 8,437,842 B2 | 5/2013 | Zhang et al. | |
| 8,532,785 B1 | 9/2013 | Crutchfield et al. | |
| 8,542,131 B2 | 9/2013 | Lund et al. | |
| 8,744,572 B1 * | 6/2014 | Greenhut | A61N 1/37288 607/4 |
| 8,923,963 B2 | 12/2014 | Bonner et al. | |
| 2002/0013613 A1 | 1/2002 | Haller et al. | |
| 2006/0135999 A1 | 6/2006 | Bodner et al. | |
| 2007/0299480 A1 | 12/2007 | Hill | |
| 2009/0299438 A1 | 12/2009 | Nolan et al. | |
| 2010/0114208 A1 * | 5/2010 | Donofrio | A61N 1/0551 607/5 |
| 2012/0016305 A1 | 1/2012 | Jollota et al. | |
| 2013/0035748 A1 | 2/2013 | Bonner et al. | |
| 2014/0121719 A1 | 5/2014 | Bonner et al. | |
| 2014/0121720 A1 | 5/2014 | Bonner et al. | |
| 2014/0214104 A1 | 7/2014 | Greenhut et al. | |
| 2014/0337922 A1 | 11/2014 | Sievert et al. | |
| 2015/0305640 A1 | 10/2015 | Reinke et al. | |
| 2015/0305641 A1 | 10/2015 | Stadler et al. | |
| 2015/0305642 A1 | 10/2015 | Reinke et al. | |

OTHER PUBLICATIONS (PCT/US2017/029759) PCT Notification of Transmittal of the International Search Report and the Written Opinion of the International Searching Authority, dated Sep. 20, 2017, 9 pages.

* cited by examiner

OPERATION OF AN EXTRACARDIOVASCULAR IMPLANTABLE CARDIOVERTER DEFIBRILLATOR (ICD) DURING IMPLANTATION OF ANOTHER MEDICAL DEVICE

TECHNICAL FIELD

This disclosure generally relates to medical devices and, more particularly, co-implantation of multiple medical devices.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of ventricular fibrillation, the use of an implantable cardioverter defibrillator (ICD) system has been shown to be beneficial at preventing SCD. An ICD system includes an ICD that is a battery powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, extracardiovascular ICD systems have been devised to provide shocks to the heart without placing electrical lead wires within the heart or attaching electrical wires directly to the heart.

Some tachyarrhythmias may be terminated by anti-tachycardia pacing (ATP) therapy. ICDs have been configured to attempt to terminate some detected tachyarrhythmias by delivery of ATP prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

To capture the heart, an extracardiovascular ICD would likely need to deliver pacing pulses having a higher magnitude than those delivered by a conventional transvenous ICD coupled to intracardiac leads due to the greater distance between the electrodes of the extracardiovascular ICD and the heart. Higher magnitude pacing pulses delivered by an extracardiovascular ICD may capture other patient tissue in addition to the heart and/or cause patient discomfort. Consequently, it has been proposed to concomitantly implant a separate cardiac pacing device with an extracardiovascular ICD configured to deliver anti-tachyarrhythmia shocks. The cardiac pacing device may be an intracardiac pacing device (IPD) configured to be wholly implanted within the heart.

SUMMARY

In general, the disclosure describes techniques for operating an extracardiovascular ICD when implanting another medical device that delivers electrical stimulation therapy. The extracardiovascular ICD provides confirmation to a clinician or other user that it is able to detect the delivery of one or more test therapy signals and, in some examples, that the one or more test therapy signals are not inappropriately detected as one or more tachyarrhythmia events. The clinician may reposition one or more components of the other implantable medical device if the extracardiovascular ICD does not detect the one or more test therapy signals. In some examples, the other medical device is a cardiac pacing device, such as an intracardiac pacing device, and the one or more test therapy signals are one or more pacing pulses, such as a test anti-tachycardia pacing (ATP) signal.

During implantation of the other medical device, a clinician may configure the extracardiovascular ICD to enter a concomitant medical device implantation mode. While in the concomitant medical device implantation mode, the extracardiovascular ICD may suspend one or both of ventricular tachyarrthmia detection or therapy delivery. The clinician implants and positions the other medical device within the patient and configures the other medical device to generate one or more test therapy signals. The extracardiovascular ICD detects the one or more test therapy signals generated by the other medical device and provides a notification that the extracardiovascular ICD has detected the one or more test therapy signals. The extracardiovascular ICD exits the concomitant medical device implantation mode and resumes normal tachyarrhythmia detection and therapy.

In one example, this disclosure describes a method including: determining, by an extracardiovascular implantable cardioverter defibrillator (ICD) implanted in a patient, whether one or more test therapy signals generated by another medical device implanted in the patient is detected; and in response to detecting the one or more test therapy signals, providing, by the extracardiovascular ICD, an indication that the extracardiovascular ICD has detected the one or more test therapy signals.

In another example, this disclosure describes an extracardiovascular ICD configured for implantation in a patient, the extracardiovascular ICD including: sensing circuitry configured to receive, via a plurality of electrodes, one or more test therapy signals generated by an intracardiac pacing device (IPD) implanted in the patient; and processing circuitry, wherein at least one of the sensing circuitry or the processing circuitry is configured to detect the one or more test therapy signals, the processing circuitry further configured to: determine whether the one or more test therapy signals are detected; and in response to detection of the one or more test therapy signals, control the extracardiovascular ICD to provide an indication that the extracardiovascular ICD has detected the one or more test therapy signals.

In another example, this disclosure describes a non-transitory computer readable medium including instructions for causing at least one programmable processor of an extracardiovascular ICD configured for implantation in a patient to: determine whether one or more test therapy signals generated by an intracardiac pacing device (IPD) implanted in the patient are detected; and in response to detection of the one or more test therapy signals, control the extracardiovascular ICD to provide an indication that the extracardiovascular ICD has detected the one or more test therapy signals.

In another example, this disclosure describes a system including: a first implantable medical device configured to deliver one or more test therapy signals via a first plurality of electrodes; and a second implantable medical device including an extracardiovascular implantable cardioverter defibrillator (ICD), the extracardiovascular ICD including:

sensing circuitry configured to receive, via a second plurality of electrodes, the one or more test therapy signals; and processing circuitry, wherein at least one of the sensing circuitry or the processing circuitry is configured to detect the one or more test therapy signals, the processing circuitry further configured to: determine whether the one or more test therapy signals are detected; and in response to detection of the one or more test therapy signals, control the second implantable medical device to provide a first indication that the second implantable medical device has detected the one or more test therapy signals.

In another example, this disclosure describes an extracardiovascular implantable cardioverter defibrillator (ICD) configured for implantation in a patient, the extracardiovascular ICD including: communication circuitry; sound generation circuitry; sensing circuitry configured to receive, via a plurality of electrodes, one or more test therapy signals generated by an intracardiac pacing device (IPD) implanted in the patient; and processing circuitry, wherein at least one of the sensing circuitry or the processing circuitry is configured to detect the one or more test therapy signals, the processing circuitry further configured to receive a telemetric command to enter a concomitant medical device implantation mode via the communication circuitry, and, in response to receiving the telemetric command: enter the concomitant medical device implantation mode; and initiate a timer, wherein, while in the concomitant medical device implantation mode, the processing circuitry is configured to: disable at least one of ventricular tachyarrhythmia detection or ventricular tachyarrhythmia therapy; determine whether the one or more test therapy signals are detected; in response to the detection of the one or more test therapy signals, control the sound generation circuitry to provide an audible indication that the extracardiovascular ICD has detected the one or more test therapy signals; and exit the concomitant medical device implantation mode and re-enable the at least one of ventricular tachyarrhythmia detection or ventricular tachyarrhythmia therapy in response to one of expiration of the timer without the detection of the one or more test therapy signals or providing the audible indication.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1A:
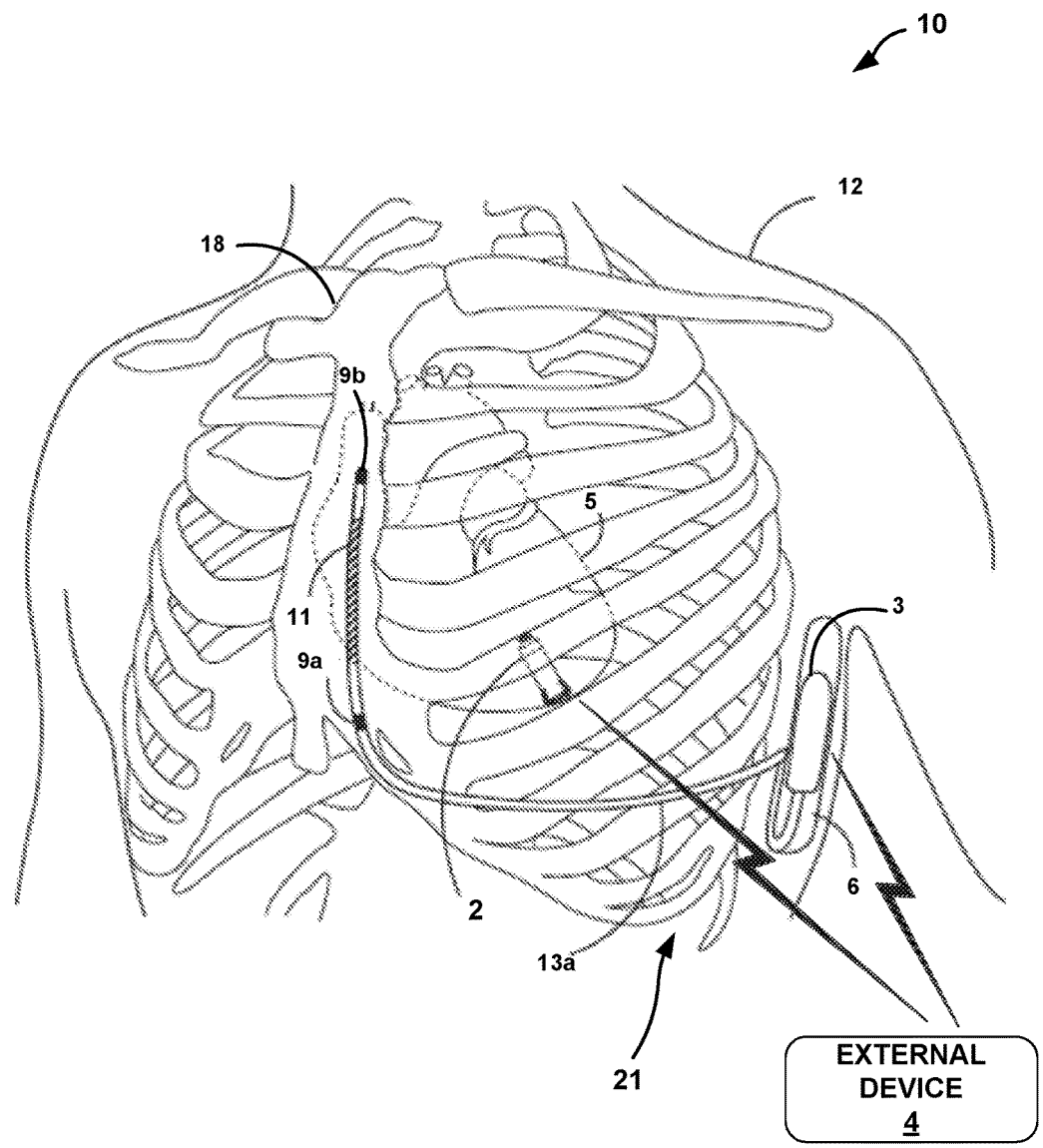
FIG. 1A is a front view of an example medical device system in conjunction with a patient according to the techniques of the disclosure.
Figure 1B:
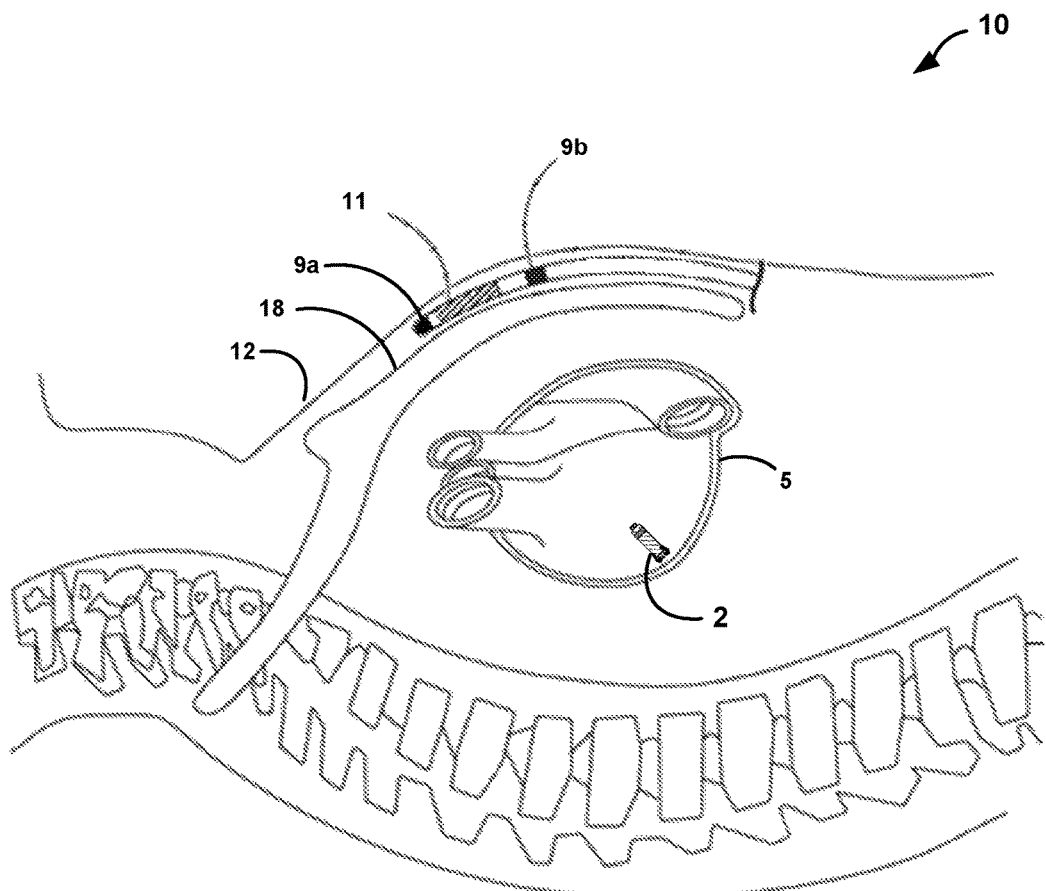
FIG. 1B is a side view of the example medical device system in conjunction with the patient according to the techniques of the disclosure.
Figure 1C:
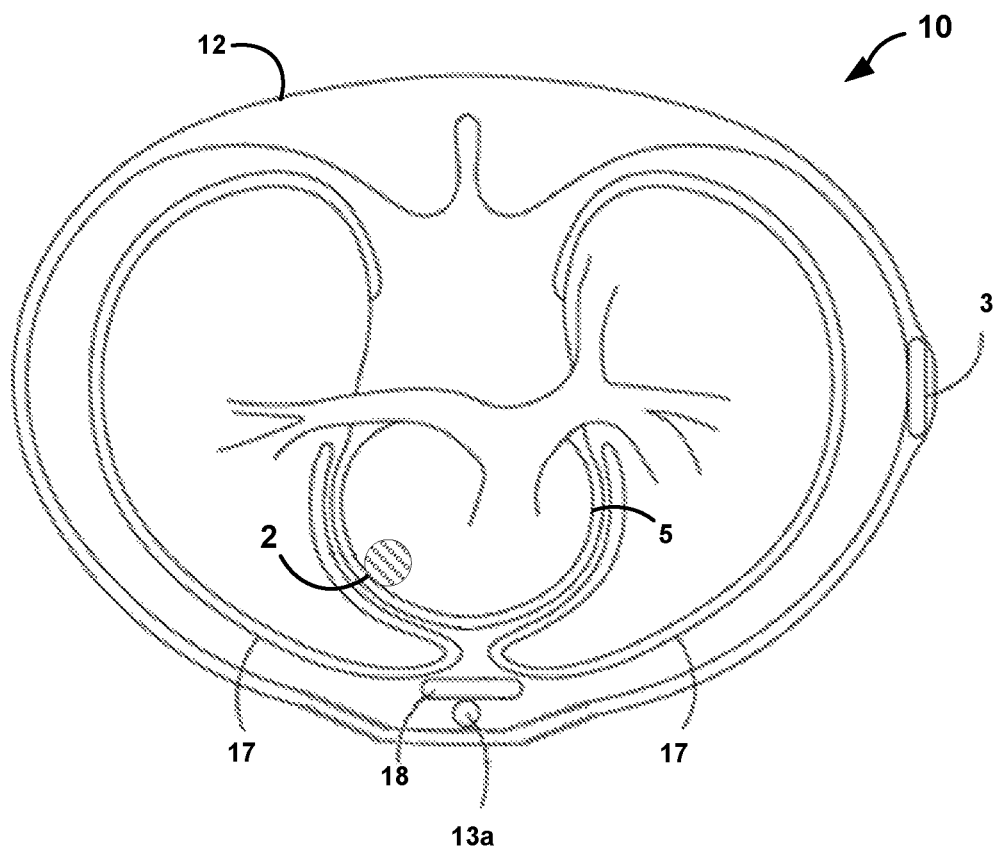
FIG. 1C is a transverse view of the example medical device system in conjunction with the patient according to the techniques of the disclosure.

FIGS. 1A-1C are conceptual drawings illustrating various views of a medical device system 10 in conjunction with a patient 12 according to the techniques of the disclosure. FIG. 1A is a front view of the medical device system 10 and the patient 12. FIG. 1B is a side view of the medical device system 10 and the patient 12. FIG. 1C is a transverse view of the medical device system 10 and the patient 12. Medical device system 10 provides cardiac therapy to the heart 5 of patient 12 and includes an intracardiac pacing device (IPD) 2 and an extracardiovascular ICD system 21. Extracardiovascular ICD system 21 includes an ICD 3 connected to a subcutaneous medical electrical lead 13. IPD 2 and ICD 3 transmit data to and receive programming instructions from an external device 4. According to the techniques of the disclosure, ICD 3 detects one or more therapy test pulses from IPD 2 and provides a notification that ICD 3 has detected the therapy test pulses.

IPD 2 is implanted within heart 5 of patient 12. In some examples, IPD 2 is a leadless cardiac pacing device (LPD). In other examples, IPD 2 may be connected to a lead, with both the IPD and lead located in the heart 5. In further examples, an epicardial pacing device configured similarly to IPD 2 is attached to the outside of the heart 5. While the techniques of the disclosure are specifically described herein as applying to an IPD, they may also be applied to any cardiac pacing device, such as an IPD, an epicardial pacing device, or a conventional transvenous pacemaker.

In the example of FIGS. 1A-1C, IPD 2 is implanted within the right ventricle of heart 5 to sense electrical activity of heart 5 and deliver pacing therapy, e.g., anti-tachycardia pacing (ATP) therapy, bradycardia pacing therapy, and/or post-shock pacing, to heart 5. In some examples, IPD 2 is attached to an interior wall of the right ventricle of heart 5 via one or more fixation elements that penetrate the tissue. These fixation elements may secure IPD 2 to the cardiac tissue and retain an electrode (e.g., a cathode or an anode) in contact with the cardiac tissue. In some examples, medical device system 10 includes additional pacing devices within respective chambers of heart 5 (e.g., right or left atrium and/or left ventricle). In some examples, a pacing device configured similarly to IPD 2 is attached to an external surface of heart 5 (e.g., in contact with the epicardium) such that the pacing device is disposed outside of heart 5.

In some examples, IPD 2 senses electrical signals using the electrodes carried on the housing of IPD 2. These electrical signals may be electrical signals generated by cardiac muscle and indicative of depolarizations and repolarizations of heart 5 at various times during the cardiac cycle. IPD 2 may analyze the sensed electrical signals to detect bradycardia or tachyarrhythmias, such as ventricular tachycardia or ventricular fibrillation. In response to detecting the detected cardiac rhythm, IPD 2 may, e.g., depending on the type of rhythm, begin to deliver therapy via the electrodes of IPD 2. For example, IPD 2 may deliver ATP therapy, bradycardia pacing therapy or post-shock pacing therapy.

ICD 3 is implanted extra-thoracically on the left side of the patient, e.g., under the skin and outside the ribcage (subcutaneously or submuscularly). ICD 3 may, in some instances, be implanted between the left posterior axillary line and the left anterior axillary line of the patient within a surgical pocket 6. ICD 3 may, however, be implanted at other extra-thoracic locations on the patient.

In the example of FIGS. 1A-1C, lead 13a is implanted in patient 12 subcutaneously or submuscularly above the sternum 18. Lead 13a may terminate in one or more electrodes 9A-9B and one or more defibrillation electrodes 11. ICD 3 provides ventricular tachyarrhythmia detection and ventricular tachyarrhythmia therapy to patient 12 via lead 13a and electrodes 9A-9B and 11.

ICD 3 may include a housing that forms a hermetic seal that protects components of the ICD 3. The housing of the ICD 3 may be formed of a conductive material, such as titanium or titanium alloy, which may function as a housing electrode (sometimes referred to as a can electrode). In other embodiments, the ICD 3 may be formed to have or may include one or more electrodes on the outermost portion of the housing. The ICD 3 may also include a connector assembly (also referred to as a connector block or header) that includes electrical feedthroughs through which electrical connections are made between conductors of lead 13a and electronic components included within the housing of the ICD 3. As will be described in further detail herein, housing may house one or more processors, memories, transmitters, receivers, sensors, sensing circuitry, therapy circuitry, power sources, and other appropriate components. The housing is configured to be implanted in a patient, such as patient 12.

IPD 2 and ICD 3 may be configured to operate completely independently of one another. In such a case, IPD 2 and ICD 3 are not capable of establishing telemetry or other communication sessions with one another to exchange information about sensing and/or therapy using one-way or two-way communication. Instead, each of IPD 2 and ICD 3 analyze the data sensed via their respective electrodes to make cardiac rhythm detection and/or therapy decisions. As such, each device does not know if the other will detect a tachyarrhythmia, if or when it will provide therapy, and the like.

In other examples, IPD 2 and ICD 3 may be configured to engage in one-way or two-way communication between IPD 2 and ICD 3. This one-way or two-way communication may be used to initiate therapy and/or confirm that therapy should be delivered. For example, one-way communication may allow ICD 3 to detect a tachyarrhythmia and transmit a communication message to IPD 2 instructing IPD 2 to deliver anti-tachycardia pacing (ATP) prior to ICD 3 delivering an anti-tachyarrhythmia shock.

As another example, two-way communication may allow confirmation of a detected tachyarrhythmia prior to delivery of any therapy. For example, ICD 3 may request a communication message from IPD 2 confirming a detected tachyarrhythmia prior to delivering an anti-tachyarrhythmia shock or IPD 2 may request a communication message from ICD 3 confirming the tachyarrhythmia prior to delivering ATP. Since the sensing vectors of the ICD 3 electrodes outside of the patient's rib cage may be different than the sensing vectors of the IPD 2 electrodes within the heart 5, confirming tachyarrhythmias using different vectors from ICD 3 and IPD 2 may reduce false positives. In some examples, IPD 2 may also be configured to deliver post-shock pacing to the heart of the patient.

In another example, IPD 2 may first detect a tachyarrhythmia eligible for an anti-tachyarrhythmia shock and/or ATP therapy. IPD 2 may transmit a communication message to ICD 3 requesting confirmation of the tachyarrhythmia. In response to detecting the tachyarrhythmia, ICD 3 may then transmit a confirmation message to IPD 2. ICD 3 may then begin charging for delivery of an anti-tachyarrhythmia shock and IPD 2 may deliver ATP prior to delivery of the shock. In some examples, ICD 3 may transmit a communication message informing IPD 2 that ATP is not effective (e.g., capturing the cardiac rhythm) and/or that a shock will be delivered and/or has been delivered.

In some cases, ICD 3 is implanted prior to implantation of IPD 2. In such cases, during the implantation of IPD 2, a clinician may perform surgical procedures that may cause heart 5 to exhibit irregular patterns, or that produce electrical signals in patient 12 that ICD 3 may detect and misinterpret as a tachyarrhythmia of heart 5. In either case, ICD 3 may misinterpret these irregular patterns or signals as a tachyarrhythmia, causing ICD 3 to inappropriately administer therapy, e.g., an anti-tachyarrhythmia shock, to heart 5.

In general, the disclosure describes techniques that may be implemented by ICD 3 and IPD 2 during implantation of IPD 2. In some examples, the techniques allow a clinician to determine, during implantation of IPD 2, that IPD 2 is positioned correctly within a patient such that ICD 3 may detect signals indicative of therapy provided by IPD 2 to the patient 12. The ability to detect delivery of therapy signals by IPD 2, e.g., delivery of ATP therapy signals, may allow ICD 3 to, for example, avoid delivering a tachyarrhythmia shock during the delivery of the therapy in response to a tachyarrhythmia that both devices have detected. The techniques may also allow the clinician to determine whether ICD 3 misinterpreted the therapy signals as one or more tachyarrhythmia events of heart 5. In some examples, the techniques may simplify the implantation procedure from the perspective of the clinician by reducing the amount of interaction with a programming device or programming software of ICD 3 during implantation of IPD 2.

For example, during implantation of IPD 2, a clinician may use external device 4 executing programming software for ICD 3 (or a dedicated external device for communicating with ICD 3) to instruct ICD 3 to enter concomitant medical device implantation mode. While in the concomitant medical device implantation mode, ICD 3 suspends one or both of ventricular tachyarrhythmia detection or delivery of tachyarrhythmia therapy to patient 12 in response to tachyarrhythmia detection. The clinician may then implant and position IPD 2 within the patient 12, and interact with IPD 2 via external device 4 and programming software for IPD 2. The clinician may instruct IPD 2 to generate one or more test therapy signals. In some examples, the one or more test therapy signals are one or more pacing pulses, such as a test ATP therapy signal or bradycardia pacing signal.

If ICD 3 detects the one or more test therapy signals generated by IPD 2, ICD 3 provides a notification that ICD 3 has detected the one or more test therapy signals. In some examples, ICD 3 provides an audible notification to the clinician. In other examples, ICD 3 generates an electrical notification via tissue conductance communication (TCC) messaging that IPD 2 detects and relays to external device 4. In other examples, ICD 3 generates an electrical notification via RF or other wireless communication that IPD 2 detects and relays to external device 4. After providing the indication, the ICD 3 exits the concomitant medical device implantation mode and resumes normal tachyarrhythmia detection and therapy.

If ICD 3 does not provide the indication in response to the one or more test therapy signals, e.g., because ICD 3 did not detect the one or more test therapy signals, the clinician may reposition IPD 2, and direct IPD 2 to provide another test therapy signal. Repositioning and delivery of the therapy signal may be repeated until ICD 3 indicates detection of the one or more test therapy signals. In this manner, the techniques of this disclosure may allow a clinician to confirm that ICD 3 is able to detect the therapy signal delivered by IPD 2 without requiring the clinician to interact with the programming software or device of the ICD.

In some examples in which ICD 3 keeps tachyarrhythmia detection enabled during the concomitant medical device implantation mode, ICD 3 may determine whether the one or more test therapy signals are inappropriately detected as one or more tachyarrhythmia events. If ICD 3 determines that the one or more test therapy signals are inappropriately detected as one or more tachyarrhythmia events, ICD 3 may provide an indication of the inappropriate tachyarrhythmia detection to the clinician. The indication may be audible, but may be distinct from the indication of successful detection of the therapy signal. Alternatively, ICD 3 provides the indication of successful detection of the therapy signal only after determining that the test signals would not interfere with the tachyarrhythmia detection scheme of ICD 3, such that there is only one notification signal. In response to the indication of inappropriate tachyarrhythmia detection, the clinician may reposition IPD 2, or change one or more parameters of the therapy signal delivered by IPD 2, or of tachyarrhythmia detection by ICD 3, to avoid the inappropriate tachyarrhythmia detection.

Accordingly, the techniques of the disclosure allow a clinician to determine, during implantation, that IPD 2 is positioned correctly within the heart such that ICD 3 may detect therapy delivered to the patient by the IPD 2, without referring to the programming software or device associated with ICD 3. In some examples, the ICD 3 notifies the clinician by providing an audible sound to indicate that ICD 3 is capable of detecting the IPD therapy such that the clinician does not need to refer to the programmer software or device associated with the ICD 3, and without requiring communication between IPD 2 and ICD 3. In other examples, the ICD 3 indicates that the ICD 3 is capable of providing an electrical notification to the IPD 2, e.g., via a TCC message, in response to detecting the IPD therapy, such that the clinician may receive this indication via the external device 4 while executing programming software associated with IPD 2. Thus, the techniques of the disclosure may reduce the number of devices or software interfaces that the clinician must consult during the implantation procedure to determine that the IPD 2 has been positioned correctly, and that ICD 3 is appropriately detecting the therapy signal delivered by IPD 2.

Figure 2A:
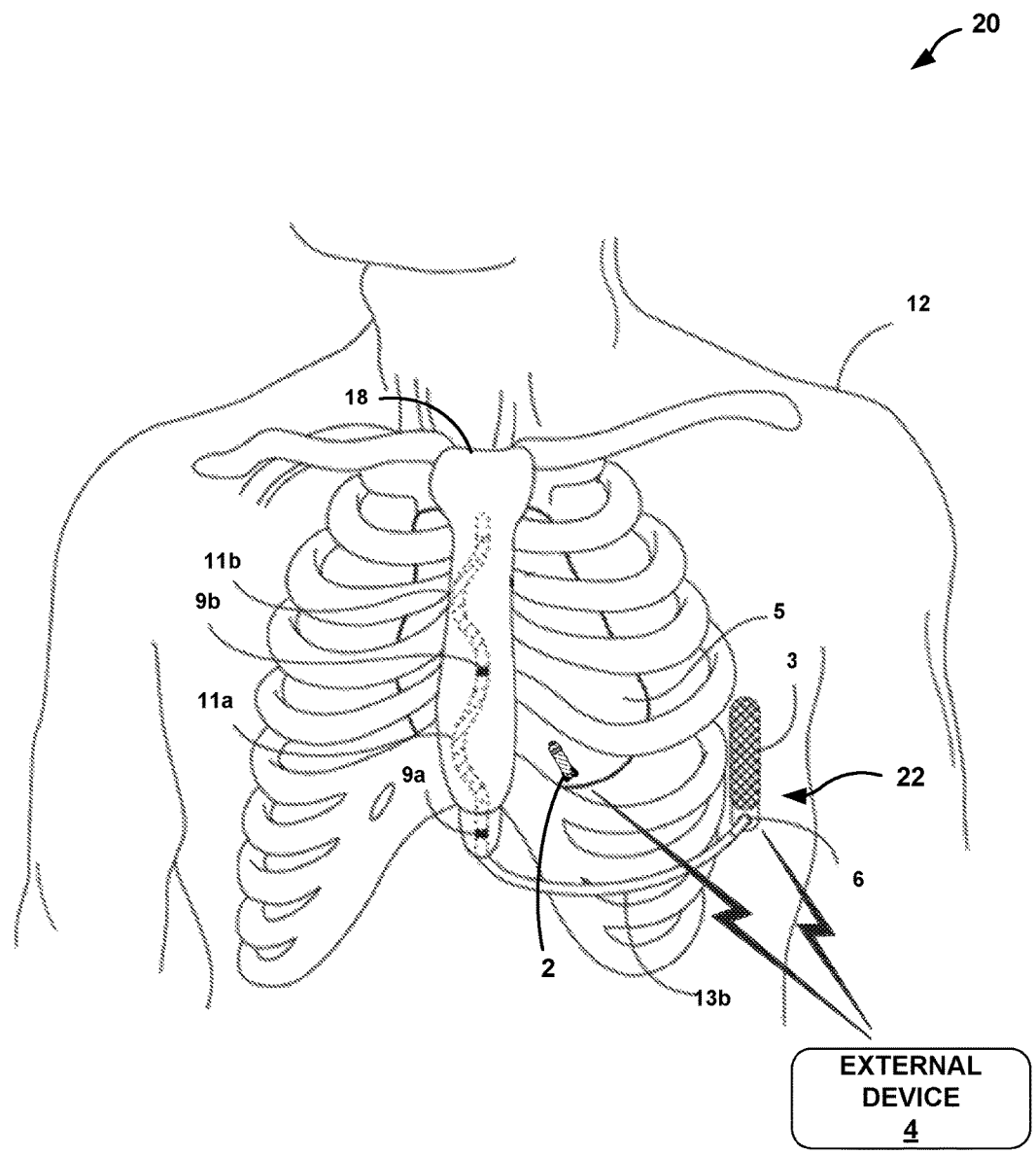
FIG. 2A is a front view of an example medical device system in conjunction with a patient according to the techniques of the disclosure.
Figure 2B:
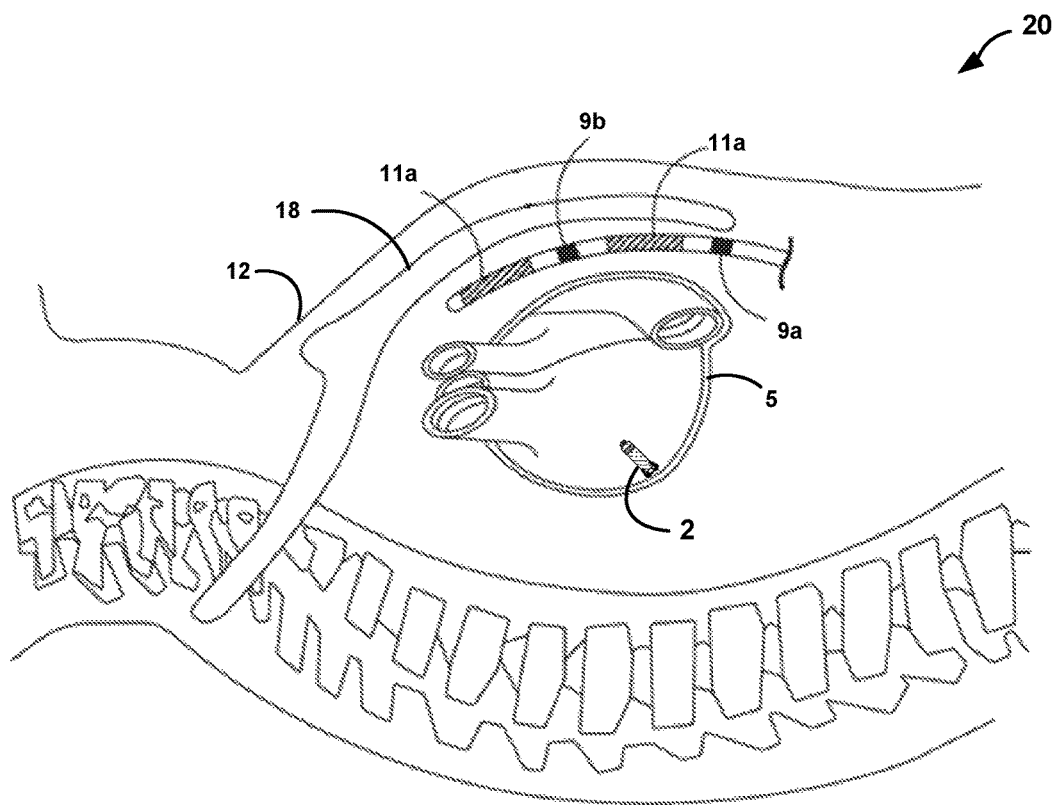
FIG. 2B is a side view of the example medical device system in conjunction with the patient according to the techniques of the disclosure.
Figure 2C:
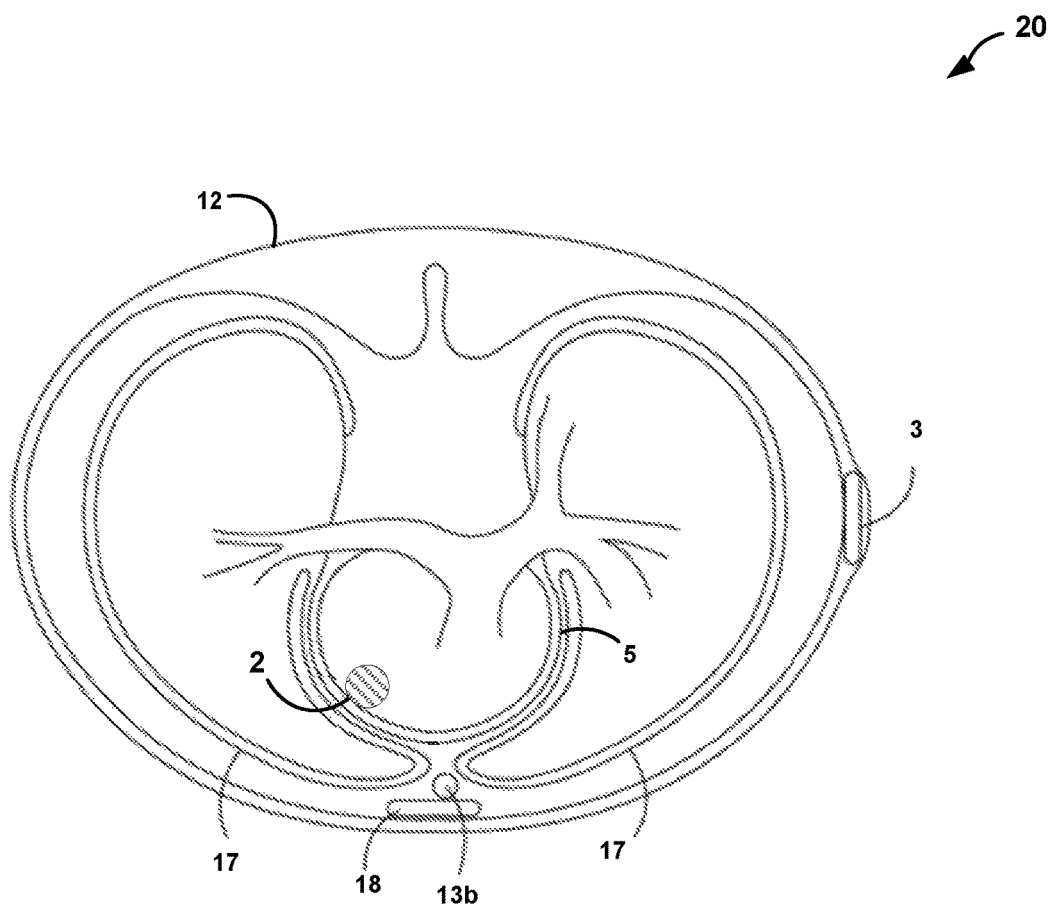
FIG. 2C is a transverse view of the example medical device system in conjunction with the patient according to the techniques of the disclosure.

FIGS. 2A-2C are conceptual drawing illustrating various views of a medical device system 20 in conjunction with a patient 12 according to the techniques of the disclosure. FIG. 2A is a front view of the medical device system 20 and the patient 12. FIG. 2B is a side view of the medical device system 20 and the patient 12. FIG. 2C is a transverse view of the medical device system 20 and the patient 12. Medical device system 20 provides cardiac therapy to the heart 5 of patient 12 and includes an intracardiac pacing device (IPD) 2 and an extracardiovascular ICD system 22. Extracardiovascular ICD system 22 includes an ICD 3 connected to a medical electrical lead 13a. Medical device system 20 functions substantially similar to the medical device system 10 of FIGS. 1A-1C. According to the techniques of the disclosure, ICD 3 detects one or more therapy test pulses from IPD 2 and provides a notification that ICD 3 has detected the therapy test pulses.

In the example medical device system 20 of FIGS. 2A-2C, this distal portion of lead 13b carrying the electrodes is implanted in patient 12 substernally below the sternum 18. Lead 13b may terminate in one or more electrodes 9A-9B and one or more defibrillation electrodes 11. ICD 3 provides tachyarrhythmia detection and anti-tachyarrhythmia therapy (e.g., ATP pacing, cardioversion/defibrillation shock and/or post-shock pacing) to patient 12 via lead 13b and electrodes 9A-9B and 11.

In general, the disclosure describes techniques that may be implemented by ICD 3 and IPD 2 during implantation of IPD 2. In some examples, the techniques allow a clinician to determine, during implantation of IPD 2, that IPD 2 is positioned correctly within a patient such that ICD 3 may detect signals indicative of therapy provided by IPD 2 to the patient 12. The ability to detect delivery of therapy signals by IPD 2, e.g., delivery of ATP therapy signals, may allow ICD 3 to, for example, avoid delivering a tachyarrhythmia shock during the delivery of the therapy in response to a tachyarrhythmia that both devices have detected. The techniques may also allow the clinician to determine whether ICD 3 misinterpreted the therapy signals as one or more tachyarrhythmia events of heart 5. In examples where ICD 3 and IPD 2 communicate with each other via TCC, the techniques may allow the clinician to determine whether TCC communication between ICD 3 and IPD 2 is successful. In some examples, the techniques may simplify the implantation procedure from the perspective of the clinician by reducing the amount of interaction with a programming device or programming software of ICD 3 during implantation of IPD 2.

Accordingly, the techniques of the disclosure allow a clinician to determine, during implantation, that IPD 2 is positioned correctly within the heart such that ICD 3 may detect therapy delivered to the patient by the IPD 2, without referring to the programming software or device associated with ICD 3. In some examples, the ICD 3 notifies the clinician by providing an audible sound to indicate that ICD 3 is capable of detecting the IPD therapy such that the clinician does not need to refer to the programmer software or device associated with the ICD 3, and without requiring telemetry communication between IPD 2 and ICD 3. In other examples, the ICD 3 indicates that the ICD 3 is capable of detecting the IPD therapy by providing an electrical notification to the IPD 2, e.g., via TCC messaging, such that the clinician may receive this indication via the external device 4 while executing programming software associated with IPD 2. Thus, the techniques of the disclosure may reduce the number of devices or software interfaces that the clinician must consult during the implantation procedure to determine that the IPD 2 has been positioned correctly, and that ICD 3 is appropriately detecting the therapy signal delivered by IPD 2.

The architectures of medical device systems 10 and 20 illustrated in FIGS. 1A-1C and 2A-2C are shown as examples. The techniques as set forth in this disclosure may be implemented in the example medical device systems 10 and 20 of FIGS. 1A-1C and 2, as well as other types of medical device systems not described specifically herein. For example, although described herein primarily in the context of examples in which the other implantable medical device being implanted with ICD 3 is an IPD, the techniques of this disclosure are not so limited. The other implantable medical device may be a cardiac pacing device having intracardiac leads, a neurostimulator, or any other implantable medical device configured to deliver a therapy signal to a patient. Nothing in this disclosure should be construed so as to limit the techniques of this disclosure to the example architectures illustrated by FIGS. 1A-1C and 2A-2C.

Figure 3:
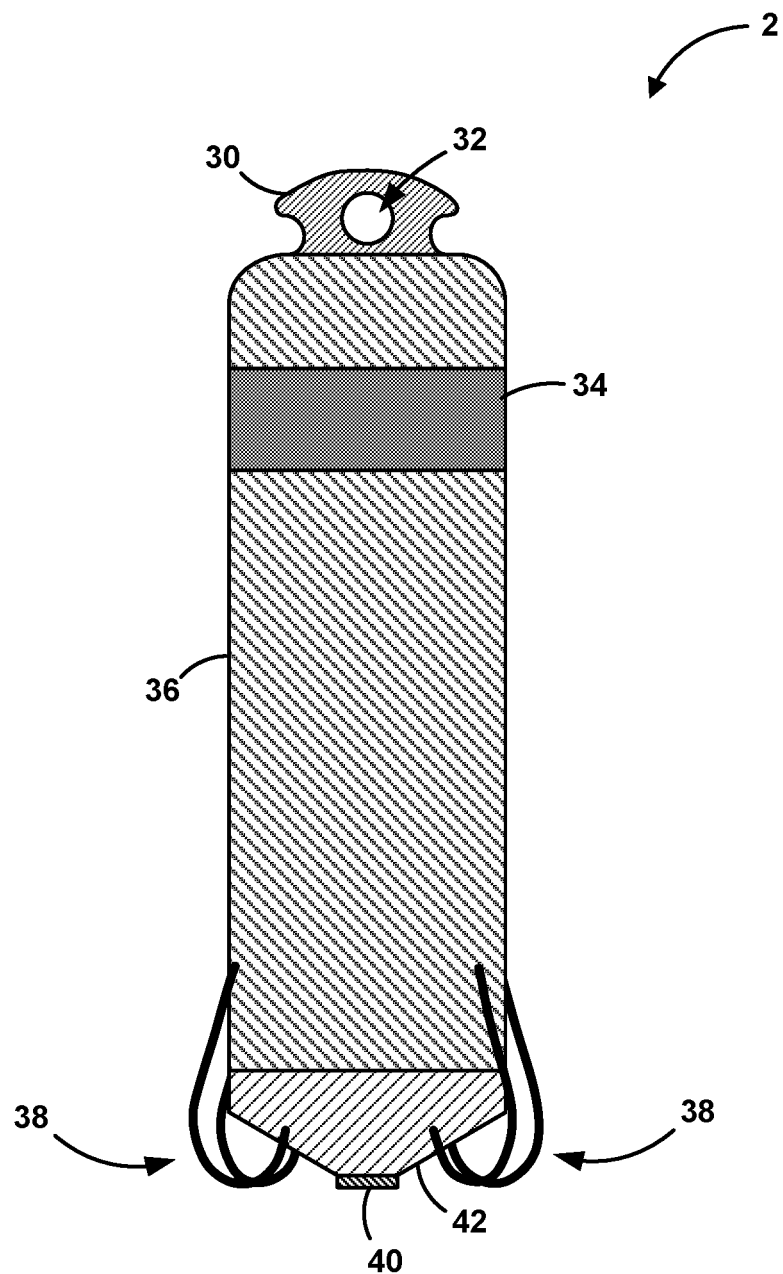
FIG. 3 is an illustration of an example configuration of an intracardiac pacing device (IPD) of FIGS. 1A-1C and 2A-2C according to the techniques of the disclosure.

FIG. 3 is an illustration of an example configuration of IPD 2 of FIGS. 1A-1C and FIGS. 2A-2C according to the techniques of the disclosure. As shown in FIG. 3, IPD 2 includes case 36, cap 42, electrode 34, electrode 40, fixation mechanisms 38, flange 30, and opening 32. Together, case 36 and cap 42 may be considered the housing of IPD 2. In this manner, case 36 and cap 42 may enclose and protect the various electrical components within IPD 2. Case 36 may enclose substantially all of the electrical components, and cap 42 may seal case 36 and create the hermetically sealed housing of IPD 2. Although IPD 2 may be described as including one or more electrodes, IPD 2 may typically include at least two electrodes (e.g., electrodes 34 and 40) to deliver an electrical signal (e.g., therapy such as one or more ATP pulses, bradycardia pacing pulses, and/or post-shock pacing pulses) and/or provide at least one sensing vector.

Electrodes 34 and 40 are carried on the housing created by case 36 and cap 42. In this manner, electrodes 34 and 40 may be considered leadless electrodes. In the example of FIG. 3, electrode 40 is disposed on the exterior surface of cap 42. In some examples, electrode 40 is a circular electrode positioned to contact cardiac tissue upon implantation. In some examples, electrode 34 is a ring or cylindrical electrode disposed on the exterior surface of case 36. Both case 36 and cap 42 may be electrically insulating. Electrode 40 functions as a cathode and electrode 34 functions as an anode, or vice versa, for delivering pacing stimulation therapy such as ATP, bradycardia pacing therapy, and/or post-shock pacing. However, electrodes 34 and 40 may be used in any stimulate on configuration. In addition, electrodes 34 and 40 may be used to detect intrinsic electrical signals from cardiac muscle. In other examples, IPD 2 may include three or more electrodes, where each electrode may deliver therapy and/or detect intrinsic signals. Therapy delivered by IPD 2, as compared with alternative devices, may be considered to be "painless" to patient 12 or even undetectable by patient 12 since the electrical stimulation occurs very close to or at cardiac muscle and at relatively low energy levels.

Fixation mechanisms 38 may attach IPD 2 to cardiac tissue. Fixation mechanisms 38 may be active fixation tines, screws, clamps, adhesive members, or any other types of attaching a device to tissue. As shown in the example of FIG. 3, fixation mechanisms 38 may be constructed of a memory material that retains a preformed shape. During implantation, fixation mechanisms 38 may be flexed forward to pierce tissue and allowed to flex back towards case 36. In this manner, fixation mechanisms 38 may be embedded within the target tissue.

Flange 30 may be provided on one end of case 36 to enable tethering or extraction of IPD 2. For example, a suture or other device may be inserted around flange 30 and/or through opening 32 and attached to tissue. In this manner, flange 30 may provide a secondary attachment structure to tether or retain IPD 2 within heart 5 if fixation mechanisms 38 fail. Flange 30 and/or opening 32 may also be used to extract IPD 2 once IPD 2 needs to be explanted (or removed) from patient 12 if a clinician deems such action necessary.

The techniques described herein are generally described with regard to an IPD such as IPD 2. In some examples, IPD 2 is configured to deliver ATP, and the one or more test therapy signals are a test ATP signal, e.g., pacing pulse train. However, other pacing signals (e.g., bradycardia pulses, CRT, or post-shock pacing pulses), or other therapy signals may be delivered by an IPD or another implantable medical device.

For example, an IPD may include a small housing that carries one or more electrodes, similar to IPD 2, and configured to be implanted within a chamber of heart 5. The IPD may also include one or more relatively short leads configured to place one or more respective electrodes at another location within the same chamber of the heart or a different chamber of the heart. In this manner, the housing of an IPD may not carry all of the electrodes used to deliver ATP or perform other functions. In other examples, each electrode of the IPD may be carried by one or more leads (e.g., the housing of the IPD may not carry any of the electrodes).

In another example, a pacing device may be configured to be implanted external to heart 5, e.g., near or attached to the epicardium of heart 5. An electrode carried by the housing of the pacing device may be placed in contact with the epicardium and/or one or more electrodes of leads coupled to the pacing may be placed in contact with the epicardium at locations suitable to provide therapy such as ATP (e.g., on external surfaces of the left and/or right ventricles). In any example, subcutaneous ICD 3 may communicate with one or more leadless or leaded medical devices implanted internal or external to heart 5.

The architecture of IPD 2 illustrated in FIG. 3 is shown for exemplary purposes only. The techniques as set forth in this disclosure may be implemented in the example IPD 2 of FIG. 3, as well as other types of IPDs or medical devices that are described herein, or not described specifically herein. Nothing in this disclosure should be construed so as to limit the techniques of this disclosure to the example architecture illustrated by FIG. 3.

Figure 4:
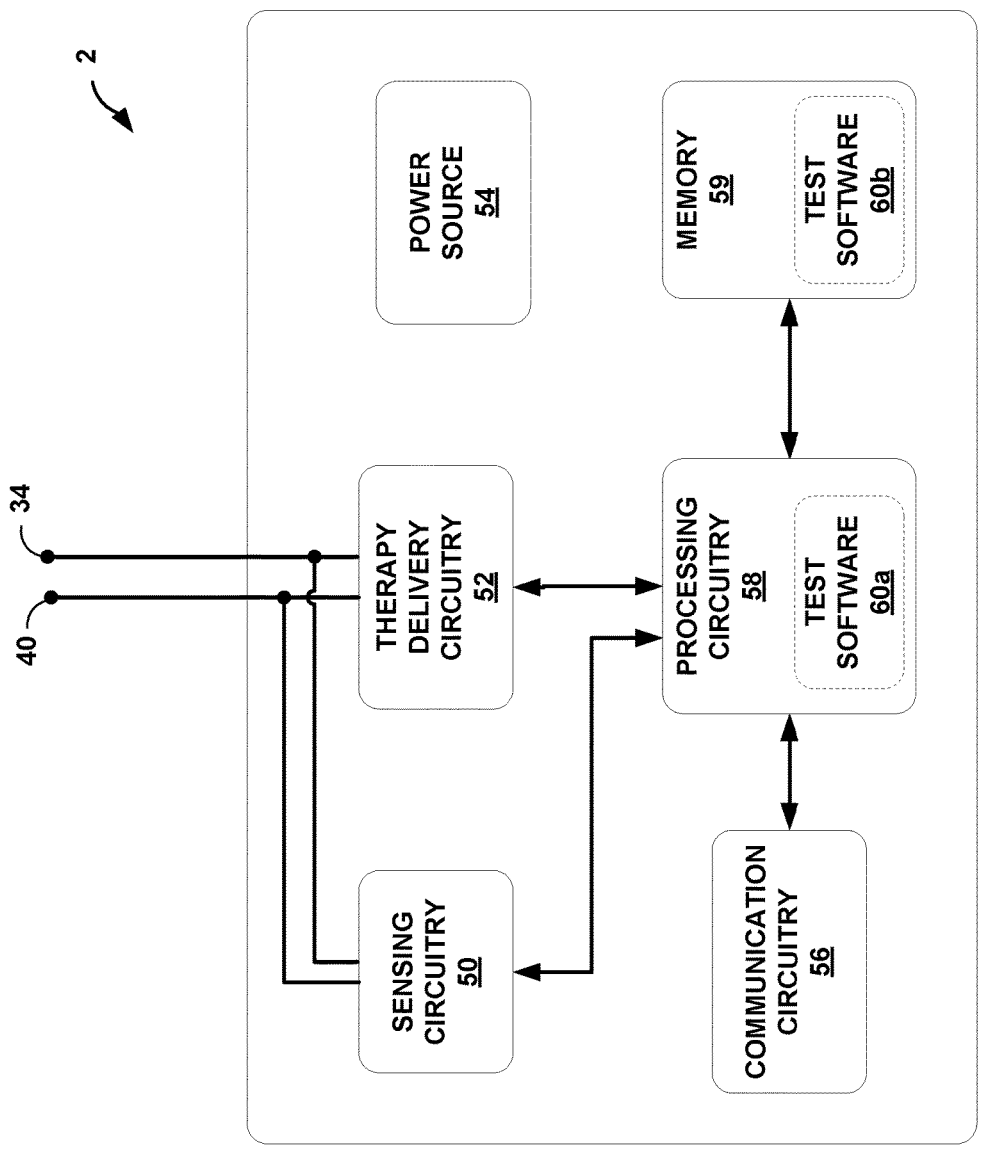
FIG. 4 is a block diagram of an example IPD of FIG. 3 according to the techniques of the disclosure.

FIG. 4 is a block diagram of an example IPD of FIG. 3 according to the techniques of the disclosure. In the illustrated example, IPD 2 includes processing circuitry 58, memory 59, communication circuitry 56, sensing circuitry 50, therapy delivery circuitry 52, and power source 54. Memory 59 includes computer-readable instructions that, when executed by processing circuitry 58, cause IPD 2 and processing circuitry 58 to perform various functions attributed to IPD 2 and processing circuitry 58 herein (e.g., detecting arrhythmias, delivering therapy, such as anti-tachycardia pacing, bradycardia pacing, and post-shock pacing therapy, and delivering test therapy signals for detection by ICD 3). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver stimulation therapy to heart 5 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 5 via electrodes 34 and 40. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

Therapy delivery circuitry 52 is electrically coupled to electrodes 34 and 40 carried on the housing of IPD 2. Although IPD 2 may only include two electrodes, e.g., electrodes 34 and 40, in other examples, IPD 2 may utilize three or more electrodes. IPD 2 may use any combination of electrodes to deliver therapy and/or detect electrical signals from patient 12. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from electrodes 34 and 40 in order to monitor electrical activity of heart 5, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 34 and 40 and converts the amplified signals to multi-bit digital signals by an ADC.

In some examples, sensing circuitry 50 performs sensing to determine heart rates or heart rate variability, or to detect arrhythmias (e.g., tachyarrhythmias or bradycardia) or other electrical signals. Sensing circuitry 50 may also include a switch to select which of the available electrodes (or electrode polarity) are used to sense the heart activity, depending upon which electrode combination, or electrode vector, is used in the current sensing configuration. In examples with several electrodes, processing circuitry 58 may select the electrodes that function as sense electrodes, i.e., select the sensing configuration, via the switch module within sensing circuitry 50. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations (e.g., P- or R-waves) and indicate the existence of the atrial depolarization (e.g., P-waves) or ventricular depolarizations (e.g., Rwaves) to processing circuitry 58. Some detection channels may be configured to detect cardiac events, such as P- or R-waves, and provide indications of the occurrences of such events to processing circuitry 58, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 58 may control the functionality of sensing circuitry 50 by providing signals via a data/address bus.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If IPD 2 is configured to generate and deliver bradycardia pacing pulses to heart 5, such counters may control the basic time intervals associated with DDD, VVI, DVI, VDD, AAI, DDI, DDDR, VVIR, DVIR, VDDR, AAIR, DDIR and other modes of pacing. Example IPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. Pat. No. 13/665,601 to Bonner et al. are both incorporated herein by reference in their entireties.

In some examples, an arrhythmia detection method may include any suitable tachyarrhythmia detection algorithms. In one example, processing circuitry 58 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 58 in other examples.

Memory 59 may be configured to store a variety of operational parameters, therapy parameters, sensed and detected data, and any other information related to the therapy and treatment of patient 12. In the example of FIG. 4, memory 58 may store sensed ECGs, e.g., associated with detected arrhythmias, and therapy parameters that define the delivery of therapy provided by therapy delivery circuitry 52. In other examples, memory 58 may act as a temporary buffer for storing data until it can be uploaded to external device 4.

In response to detecting a tachyarrhythmia, processing circuitry 58 may control therapy delivery circuitry 52 to deliver ATP therapy to heart 5 via electrodes 34 and 40. The ATP therapy may be defined by a set of parameters. These parameters may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHY-CARDIA PACING (ATP) AND HIGH VOLTAGE THERAPY FOR TREATING VENTRICULAR ARRHYTHMIAS," and issued on May 10, 2005, the entire content of which is incorporated herein by reference.

In some examples, memory 59 and processing circuitry 58 stores and executes, respectively, ICD therapy test software 60. During an implantation procedure, a clinician uploads ICD therapy test software 60b to memory 59. After positioning IPD 2, the clinician may use external device 4 to instruct IPD 2 to execute ICD therapy test software 60 on processing circuitry 58. In some examples, IPD 2 receives these instructions from external device 4 via communication circuitry 56. Processing circuitry 58, executing ICD therapy test software 60, causes therapy delivery circuitry 52 to provide one or more therapy test pulses, e.g., ATP or other pacing pulses, via electrodes 34 and 40 to the heart 5 of patient 12. As is discussed in further detail below, ICD 3 detects the therapy test pulses (or other test therapy signal) and provides a notification that it has successfully detected the therapy test pulses. The clinician, upon receiving this notification, may conclude that the IPD 2 has been positioned properly within heart 5 such that it may operate in conjunction with ICD 3 to provide cardiac therapy to patient 12. In some examples, ICD 3 provides an audible notification to the clinician. In other examples, ICD 3 generates an electrical notification via TCC messaging that sensing circuitry 50 of IPD 2 detects via electrodes 34 and 40. In this example, IPD 2 may relay the notification to external device 4 via communication circuitry 56.

Communication circuitry 56 includes any suitable circuitry, firmware, software, or any combination thereof for communicating with another device, such as external device 4 of FIGS. 1A-1C and 2A-2C. For example, communication circuitry 56 may include one or more antennae, modulation and demodulation circuitry, filters, amplifiers, or the like for radio frequency communication with other devices, such as external device 4. Under the control of processing circuitry 58, communication circuitry 56 may receive downlink telemetry from and send uplink telemetry to external device 4 with the aid of an antenna, which may be internal and/or external. Processing circuitry 58 may provide the data to be uplinked to external device 4 and the control signals for the telemetry circuit within communication circuitry 56, e.g., via an address/data bus. In some examples, communication circuitry 56 may provide received data to processing circuitry 58 via a multiplexer.

In some examples, IPD 2 uses communication circuitry 56 to communicate with ICD 3. To facilitate communication between IPD 2 and ICD 3, communication circuitry 56 may be connected to one or more electrodes 34 and 40 (connection not depicted) such that communication circuitry 56 may generate, transmit, and receive TCC signals to and from ICD 3 via the electrodes. In this example, communication circuitry 56 uses TCC to transmit messages to ICD 3 through the body of patient 12. In other examples, communication circuitry 56 includes an antenna for communicating wirelessly with ICD 3.

Power source 54 may be any type of device that is configured to hold a charge to operate the circuitry of IPD 2. Power source 54 may be provided as a rechargeable or non-rechargeable battery. In other example, power source 54 may incorporate an energy scavenging system that stores electrical energy from movement of IPD 2 within patient 12.

Accordingly, the techniques of the disclosure allow a clinician to determine, during implantation, that IPD 2 is positioned correctly within the heart such that ICD 3 may detect therapy delivered to the patient by the IPD 2, without referring to the programming software or device associated with ICD 3. In some examples, the ICD 3 notifies the clinician by providing an audible sound to indicate that ICD 3 is capable of detecting the IPD therapy such that the clinician does not need to refer to the programmer software or device associated with the ICD 3, and without requiring telemetry communication between IPD 2 and ICD 3. In other examples, the ICD 3 indicates that the ICD 3 is capable of detecting the IPD therapy by providing an electrical notification to the IPD 2 via TCC messaging, such that the clinician may receive this indication via the external device 4 while executing programming software associated with IPD 2. Thus, the techniques of the disclosure may reduce the number of devices or software interfaces that the clinician must consult during the implantation procedure to determine that the IPD 2 has been positioned correctly, and that ICD 3 is appropriately detecting the therapy signal delivered by IPD 2.

The architecture of IPD 2 illustrated in FIG. 4 is shown for exemplary purposes only. The techniques as set forth in this disclosure may be implemented in the example IPD 2 of FIG. 4, as well as other types of IPDs not described specifically herein. Nothing in this disclosure should be construed so as to limit the techniques of this disclosure to the example architecture illustrated by FIG. 4.

Figure 5:
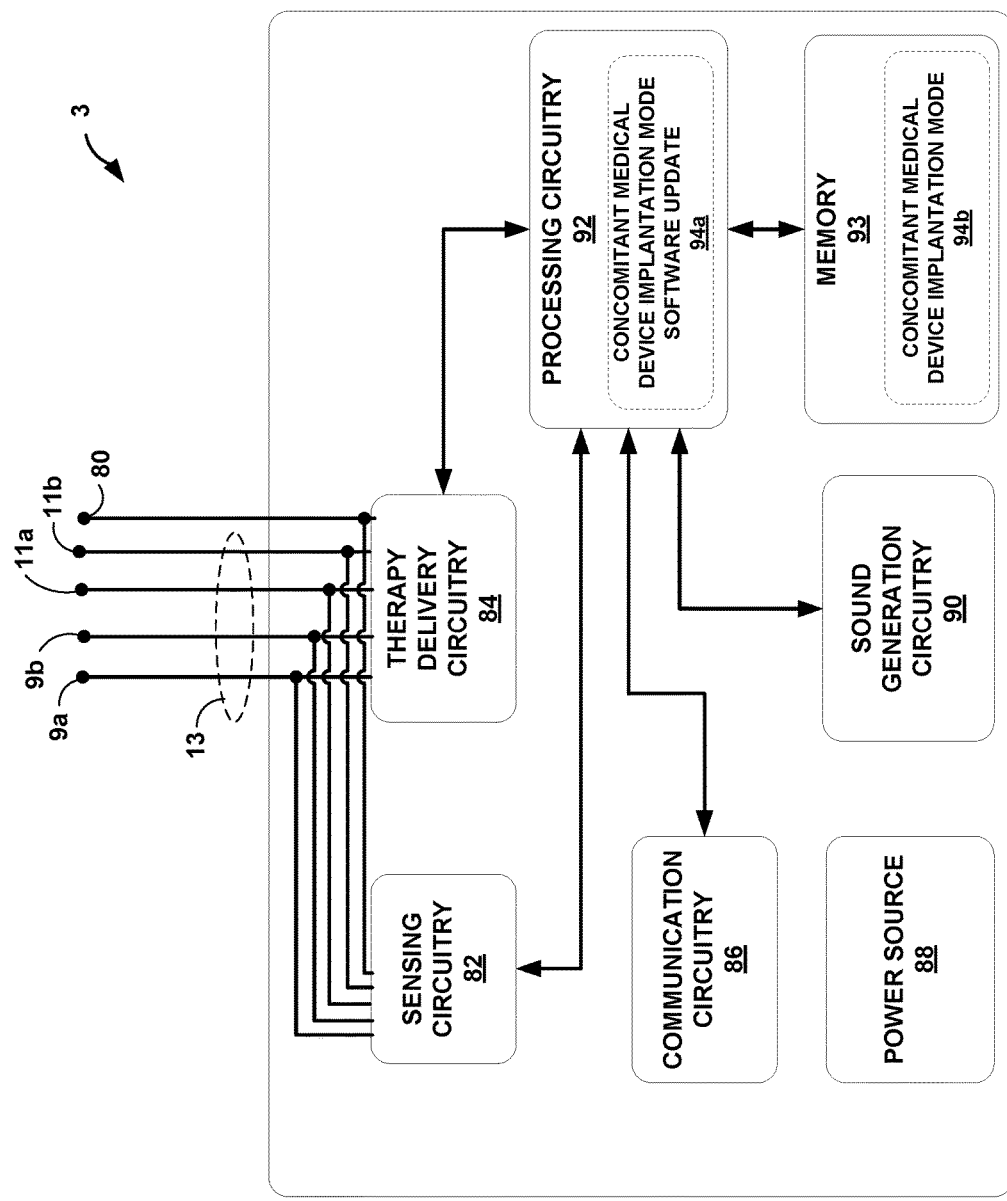
FIG. 5 is a block diagram of an example extracardiovascular ICD of FIGS. 1A-1C and 2A-2C according to the techniques of the disclosure.

FIG. 5 is a block diagram of an example ICD 3 of FIGS. 1A-1C and 2A-2C according to the techniques of the disclosure. In the example of FIG. 5, ICD 3 includes processing circuitry 92, memory 93, sensing circuitry 82, therapy delivery circuitry 84, communication circuitry 86, power source 88, and sound generation circuitry 90.

Power source 88 may be any type of device that is configured to hold a charge to operate the circuitry of ICD 3. Power source 88 may be provided as a rechargeable or non-rechargeable battery. In other example, power source 88 may incorporate an energy scavenging system that stores electrical energy from movement of ICD 3 within patient 12.

Sensing circuitry 82 is electrically coupled to some or all of electrodes 9a, 9b, and 11, via the conductors of lead 13 and one or more electrical feedthroughs, or to the housing electrode 80 via conductors internal to the housing of ICD 3. Sensing circuitry 82 is configured to obtain signals sensed via one or more combinations of electrodes 9a, 9b, and 11 and the housing electrode 80 of ICD 3 and process the obtained signals.

The components of sensing circuitry 82 may be analog components, digital components or a combination thereof. Sensing circuitry 82 may, for example, include one or more sense amplifiers, filters, rectifiers, threshold detectors, analog-to-digital converters (ADCs), or the like. Sensing circuitry 82 may convert the sensed signals to digital form and provide the digital signals to processing circuitry 92 for processing or analysis. For example, sensing circuitry 82 may amplify signals from the sensing electrodes and convert the amplified signals to multi-bit digital signals by an ADC. Sensing circuitry 82 may also compare processed signals to a threshold to detect the existence of atrial or ventricular depolarizations (e.g., P- or R-waves) and indicate the existence of the atrial depolarization (e.g., P-waves) or ventricular depolarizations (e.g., R waves) to processing circuitry 92.

Processing circuitry 92 may process the signals from sensing circuitry 82 to monitor electrical activity of the heart of the patient. Processing circuitry 92 may store signals obtained by sensing circuitry 82 as well as any generated EGM waveforms, marker channel data or other data derived based on the sensed signals in memory 93. Processing circuitry 92 may analyze the EGM waveforms and/or marker channel data to detect cardiac events (e.g., tachycardia). In response to detecting the cardiac event, processing circuitry 92 may control therapy delivery circuitry 84 to deliver the desired therapy to treat the cardiac event, e.g., an anti-tachyarrhythmia shock.

Therapy delivery circuitry 84 is configured to generate and deliver therapy to the heart. Therapy delivery circuitry 84 may include one or more pulse generators, capacitors, and/or other components capable of generating and/or storing energy to deliver as anti-tachyarrhthmia shocks or other therapeutic signals. Therapy delivery circuitry 84 may include a switch module to select which of the available electrodes are used to deliver the therapy. The switch module may include a switch array, switch matrix, multiplexer, or any other type of switching device suitable to selectively couple electrodes to therapy delivery circuitry 84. Processing circuitry 92 may select the electrodes to function as therapy electrodes, or the therapy vector, via the switch module within therapy delivery circuitry 84. In instances in which defibrillation segments 11a and 11b are each coupled to separate conductors, processing circuitry 92 may be configured to selectively couple therapy delivery circuitry 84 to any two or more of electrode(s) 11 and a housing electrode 80 provided by the housing of ICD 3. In some instances, the same switch module may be used by both therapy delivery circuitry 84 and sensing circuitry 82. In other instances, each of sensing circuitry 82 and therapy delivery circuitry 84 may have separate switch modules.

In some examples, ICD 3 uses communication circuitry 86 to communicate with IPD 2. To facilitate communication between IPD 2 and ICD 3, communication circuitry 86 may be connected to one or more electrodes 9a, 9b, and 11 (connection not depicted) such that communication circuitry 86 may generate, transmit, and receive TCC signals to and from IPD 2 via the electrodes. In this example, communication circuitry 86 uses TCC to transmit messages to IPD 2 through the body of patient 12. In other examples, communication circuitry 86 includes an antenna for communicating wirelessly with IPD 2.

In the case of cardioversion or defibrillation therapy, e.g., cardioversion or defibrillation shocks (individually or collectively referred to as "anti-tachyarrhythmia shocks"), processing circuitry 92 controls therapy delivery circuitry 84 to generate shocks having any of a number of waveform properties, including leading-edge voltage, tilt, delivered energy, pulse phases, and the like. Therapy delivery circuitry 84 may, for instance, generate monophasic, biphasic, or multiphasic waveforms. Additionally, therapy delivery circuitry 84 may generate cardioversion or defibrillation waveforms having different amounts of energy. Delivering cardioversion or defibrillation shocks from the substernal space, e.g., from electrode segment(s) 11 substantially within the anterior mediastinum of patient 12 as illustrated in FIGS. 2A-2C, may reduce the amount of energy that needs to be delivered to defibrillate the heart. When lead 13 is implanted in the substernal space, therapy delivery circuitry 84 may generate and deliver cardioversion or defibrillation shocks having energies of less than 65 J, between 40-50 J, between 35-65 J, and in some instances less than 35 J. When lead 13 is implanted subcutaneously or submuscularly, ICD 3 may generate and deliver cardioversion or defibrillation shocks having energies around 65-80 J.

In some examples, therapy delivery circuitry 84 generates defibrillation waveforms having different tilts. In the case of a biphasic defibrillation waveform, therapy delivery circuitry 84 uses a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide substernal defibrillation via defibrillation electrode segment(s) 11.

ICD 3 further includes sound generation circuitry 90. Sound generation circuitry 90 generates an audible notification to the clinician that ICD 2 has detected the one or more test therapy signals from IPD 2. In some examples, sound generation circuitry 90 is a speaker, such as a piezoelectric speaker. In some examples, sound generation circuitry 90 provides an audible tone, beep, buzz, pattern, or verbal communication.

During an implantation procedure, a clinician uses an external device 4 associated with ICD 3 to instruct ICD 3 to enter a concomitant medical device implantation mode. In some examples, external device 4 installs a concomitant medical device implantation mode software update 94 into memory 93 of ICD 3. Processing circuitry 92 executes concomitant medical device implantation mode software update 94. In some examples, concomitant medical device implantation mode software update 94 instructs processing circuitry 92 to disable therapy provided to patient 12 by therapy delivery circuitry 84. In other examples, concomitant medical device implantation mode software update 94 additionally or alternatively causes processing circuitry 92 to disable ventricular tachycardia or fibrillation detection by sensing circuitry 82. In other words, in some cases, processing circuitry 92 disables therapy provided to patient 12 while leaving ventricular tachycardia or fibrillation detection enabled during the concomitant medical device implantation mode. In some examples, processing circuitry 92 starts a countdown timer upon entering the concomitant medical device implantation mode.

While ICD 3 is operating in concomitant medical device implantation mode, the clinician may implant IPD 2 into patient 12. After positioning IPD 2 within the heart 5 of patient 12, the clinician instructs IPD 2 to deliver one or more test therapy signals to patient 12. If IPD 2 is positioned properly, ICD 3 detects the one or more test therapy signals via sensing circuitry 82. For example, sensing circuitry 82 detects cardiac signals via one or more electrodes 9a, 9b, and 11. In some examples, sensing circuitry 82 performs amplification of these signals. Sensing circuitry 82 compares the processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 92. In some examples, sensing circuitry 82 of ICD 3 detects the one or more test therapy signals according to techniques for pacing pulse detectors as described in more detail in U.S. Patent App. Pub. No. 2015/0305640 to Reinke et al., published on Oct. 29, 2015 and entitled, "IMPLANTABLE MEDICAL DEVICE (IMD) SENSING MODIFICATIONS RESPONSIVE TO DETECTED PACING PULSES"; U.S. Patent App. Pub. No. 2015/0305641 to Stadler et al., published on Oct. 29, 2015 and entitled, "IMPLANTABLE CARDIOVERTER-DEFIBRILLATOR (ICD) TACHYARRHYTHMIA DETECTION MODIFICATIONS RESPONSIVE TO DETECTED PACING"; and U.S. Patent App. Pub. No. 2015/0305642 to Reinke et al., published on Oct. 29, 2015 and entitled, "PACE PULSE DETECTOR FOR AN IMPLANTABLE MEDICAL DEVICE," each of which is incorporated by reference herein in its entirety.

Processing circuitry 92 determines whether the signals identified by sensing circuitry 82 are cardiac events requiring ventricular tachyarrhythmia therapy, or are pacing signals, such as ATP therapy, provided by IPD 2. In some examples, processing circuitry 92 examines the frequency of the signal to determine whether it is a pacing pulse or a cardiac signal. In other words, if a pacing signal is delivered by IPD 2 and is of an amplitude that triggers a sensed event by sensing circuitry 82, processing circuitry 92 may reject the event as a cardiac signal because it has the signature of ATP therapy. Therefore, processing circuitry 92 would not include the event within ventricular tachyarrhythmia detection. In further examples, sensing circuitry 82 includes one or more filters to discard events having frequencies commonly associated with ATP therapy such that the events do not affect the threshold or response of the sense amplifier of sensing circuitry 82. Accordingly, processing circuitry 92 operates to ensure that ICD 3 provides reliable ventricular tachyarrhythmia detection and therapy in the presence of ATP therapy provided by IPD 2.

In one example, upon detecting the one or more test therapy signals, processing circuitry 92 instructs sound generation circuitry 90 to provide an audible notification to the clinician that ICD 3 has detected the one or more test therapy signals. In another example, upon detecting the one or more test therapy signals, processing circuitry 92 instructs therapy delivery circuitry 84 to generate an electrical notification that is transmitted, via one or more of electrodes 9, 11, or 80, into patient 12. In this example, IPD 2 senses the electrical notification via one or more of electrodes 34 and 40. IPD 2 transmits a telemetric notification to external device 4, e.g., via its communication circuitry 56, whereupon the clinician may receive the notification. Upon receiving the notification, the clinician may determine that IPD 2 is positioned correctly such that ICD 3 is capable of detecting when IPD 2 is administering therapy to patient 12. Accordingly, ICD 3 may synchronize its therapy with the therapy provided by IPD 2 without transmitting telemetry between ICD 3 and IPD 2.

In some examples, ICD 3 and IPD 2 may communicate with one another via TCC messages. While ICD 3 is operating in concomitant medical device implantation mode, IPD 2 enter into a test TCC mode. While in this mode, IPD 2 transmits a test therapy pacing signal followed by a test TCC message. In response to receiving the TCC message, ICD 3 may communicate a notification indicating its successful receipt of the TCC message. Upon receiving the notification, the clinician may determine that TCC is functioning adequately between ICD 3 and IPD 2.

In some examples, upon transmitting the notification that ICD 3 has detected the one or more test therapy signals, ICD 3 will exit the concomitant medical device implantation mode. In some examples, if ICD 3 fails to detect one or more test therapy signals prior to the expiration of the countdown timer, ICD 3 will exit the concomitant medical device implantation mode. In either case, upon exiting the concomitant medical device implantation mode, ICD 3 removes the concomitant medical device implantation mode software update 94 from memory 93 such that ICD 3 may not inadvertently enter this mode after the implantation procedure. Processing circuitry 92 resumes normal operation of ICD 3, such as enabling one or both of ventricular tachyarrhythmia therapy provided by therapy delivery circuit 84 and/or ventricular tachyarrhythmia detection provided by sensing circuitry 82.

Accordingly, the techniques of the disclosure allow a clinician to determine, during implantation, that IPD 2 is positioned correctly within the heart such that ICD 3 may detect therapy delivered to the patient by the IPD 2, without referring to the programming software or device associated with ICD 3. In some examples, the ICD 3 notifies the clinician by providing an audible sound to indicate that ICD 3 is capable of detecting the IPD therapy such that the clinician does not need to refer to the programmer software or device associated with the ICD 3, and without requiring telemetry communication between IPD 2 and ICD 3. In other examples, the ICD 3 indicates that the ICD 3 is capable of detecting the IPD therapy by providing an electrical notification to the IPD 2 via TCC messaging, such that the clinician may receive this indication via the external device 4 while executing programming software associated with IPD 2. Thus, the techniques of the disclosure may reduce the number of devices or software interfaces that the clinician must consult during the implantation procedure to determine that the IPD 2 has been positioned correctly, and that ICD 3 is appropriately detecting the therapy signal delivered by IPD 2.

Processing circuitry 92 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 93 may include computer-readable instructions that, when executed by processing circuitry 92 or another component of ICD 3, cause one or more components of ICD 3 to perform various functions attributed to those components in this disclosure. Memory 93 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

In other embodiments, ICD 3 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

The architecture of ICD 3 illustrated in FIG. 5 is shown for exemplary purposes only. The techniques as set forth in this disclosure may be implemented in the example ICD 3 of FIG. 5, as well as other types of ICDs not described specifically herein. Nothing in this disclosure should be construed so as to limit the techniques of this disclosure to the example architecture illustrated by FIG. 5.

Figure 6:
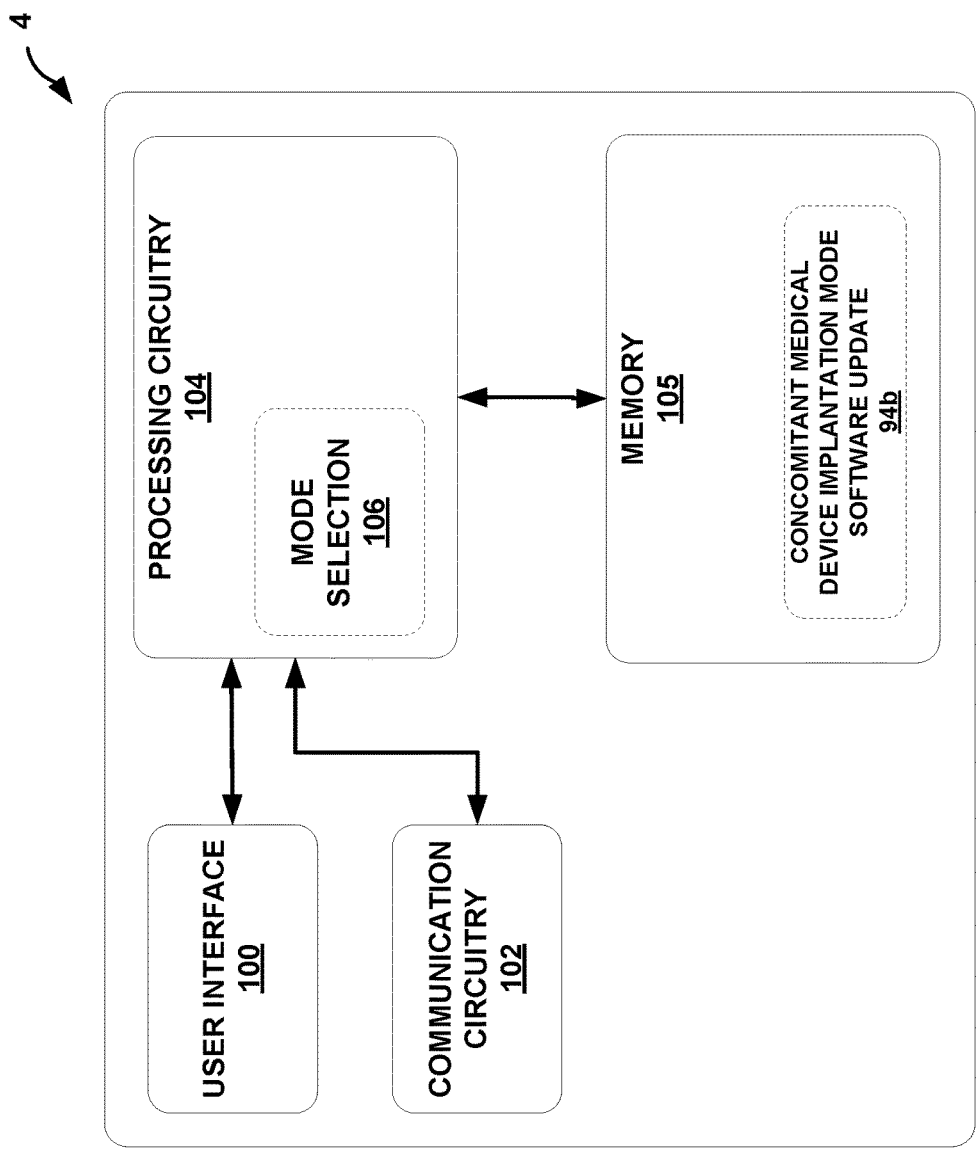
FIG. 6 is a block diagram of an example external device of FIGS. 1A-1C and 2A-2C according to the techniques of the disclosure.

FIG. 6 is a block diagram of an example external device 4 of FIGS. 1A-1C and 2A-2C according to the techniques of the disclosure. External device 4 is used to interface with an implanted medical device, such as one or both of IPD 2 and ICD 3 of FIG. 1, using a communication scheme, usually called telemetry. In some examples external device 4 is configured to program the implanted medical device. In other examples, external device 4 is configured to interrogate the implanted medical device to obtain information or telemetric data from the implanted medical device. External device 4 is used for any number of tasks associated with an implanted medical device, including, but not limited to, obtaining information about the condition, state or status of the implanted medical device, obtaining information about patient 12, including information related to the treatment intended to be provided by the implanted medical device, sending information directed or, at least in part, specifying the treatment parameters and conditions being or to be provided by the implanted medical device, or sending or updating maintenance information concerning the implanted medical device. In short, external device 4 facilitates communication between a clinician and an implanted medical device after implantation of the implanted medical device.

External device 4 includes communication circuitry 102 containing components necessary for communicating telemetry data with an implanted medical device. External device 4 further includes a user interface 100. A clinician may use user interface 100 to send and receive commands to ICD 3 and IPD 2 via external device 4. Typically, user interface 100 includes control inputs and information outputs. Control inputs can consist of buttons, discrete or soft, screen inputs (cursor, mouse, trackball, pointer, etc.), text input, voice input, and other well known input techniques. Information outputs may include well known outputs such as visual, auditory or tactile, including lights, screens, including liquid crystal display screens or light emitting diode displays, icons, text, synthesized voice, graphs, colors and the like.

External device 4 further includes a memory 105 for storing programming instructions for generating and processing the user interface and processing information received from the implanted medical device and generating commands or information to be sent to the implanted medical device. Memory 105 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 104 executes the programming instructions stored in memory 105. Processing circuitry 104 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 104 may include multiple components, such as any combination of one or more microprocessors, one or more controllers, one or more DSPs, one or more ASICs, or one or more FPGAs, as well as other discrete or integrated logic circuitry. The functions attributed to processing circuitry 104 herein may be embodied as software, firmware, hardware or any combination thereof.

Communication circuitry 102 includes any suitable circuitry, firmware, software, or any combination thereof for communicating with another device, such as IPD 2 and ICD 3 of FIGS. 1A-1C and 2A-2C. For example, communication circuitry 102 may include one or more antennae, modulation and demodulation circuitry, filters, amplifiers, or the like for radio frequency communication with other devices, such as such as IPD 2 and ICD 3. Under the control of processing circuitry 104, communication circuitry 102 may receive downlink telemetry from and send uplink telemetry to other devices with the aid of an antenna, which may be internal and/or external. Processing circuitry 104 may provide the data to be uplinked to other devices and the control signals for the telemetry circuit within communication circuitry 102, e.g., via an address/data bus. In some examples, communication circuitry 104 may provide received data to processing circuitry 104 via a multiplexer.

In some examples, external device 4 is representative one external device configured to communicate with IPD 2, and another external device configured to communicate with ICD 3. In further examples, external device 4 includes one or more software programs such that external device 4 is configured to communicate with both IPD 2 and ICD 3.

During implantation of IPD 2, a clinician, via an external device 4 configured to communicate with ICD 3, instructs ICD 3 to enter into a concomitant medical device implantation mode by selecting the mode via user interface 100 of external device 4. Processing circuitry 104 retrieves a concomitant medical device implantation mode software update 94*b* from memory 105 and transmits the software update 94*b* to ICD 3 for installation via communication circuitry 102.

During implantation, the clinician, via an external device 4 configured to communicate with IPD 2, instructs IPD 2 to generate one or more test therapy signals. As described above, ICD 3 generates a notification to indicate to the clinician that it has successfully detected the one or more test therapy pulses. In one example, the notification is an audible tone generated by ICD 3. In another example, ICD 3 electrically transmits the notification, which IPD 2 detects and forwards the notification to the external device 4 configured to communicate with IPD 2, whereupon the clinician may receive the notification.

After successful implantation of the IPD 2, as described above, the clinician, via the external device 4 configured to communicate with ICD 3, instructs ICD 3 to exit the concomitant medical device implantation mode by deselecting the mode via user interface 100 of external device 4. Processing circuitry 104 instructs ICD 3 to uninstall and remove the ICD implantation mode software update via communication circuitry 102.

The architecture of external device 4 illustrated in FIG. 6 is shown for exemplary purposes only. The techniques as set forth in this disclosure may be implemented in the example external device of FIG. 6, as well as other types of external devices not described specifically herein. Nothing in this disclosure should be construed so as to limit the techniques of this disclosure to the example architecture illustrated by FIG. 6.

Figure 7:
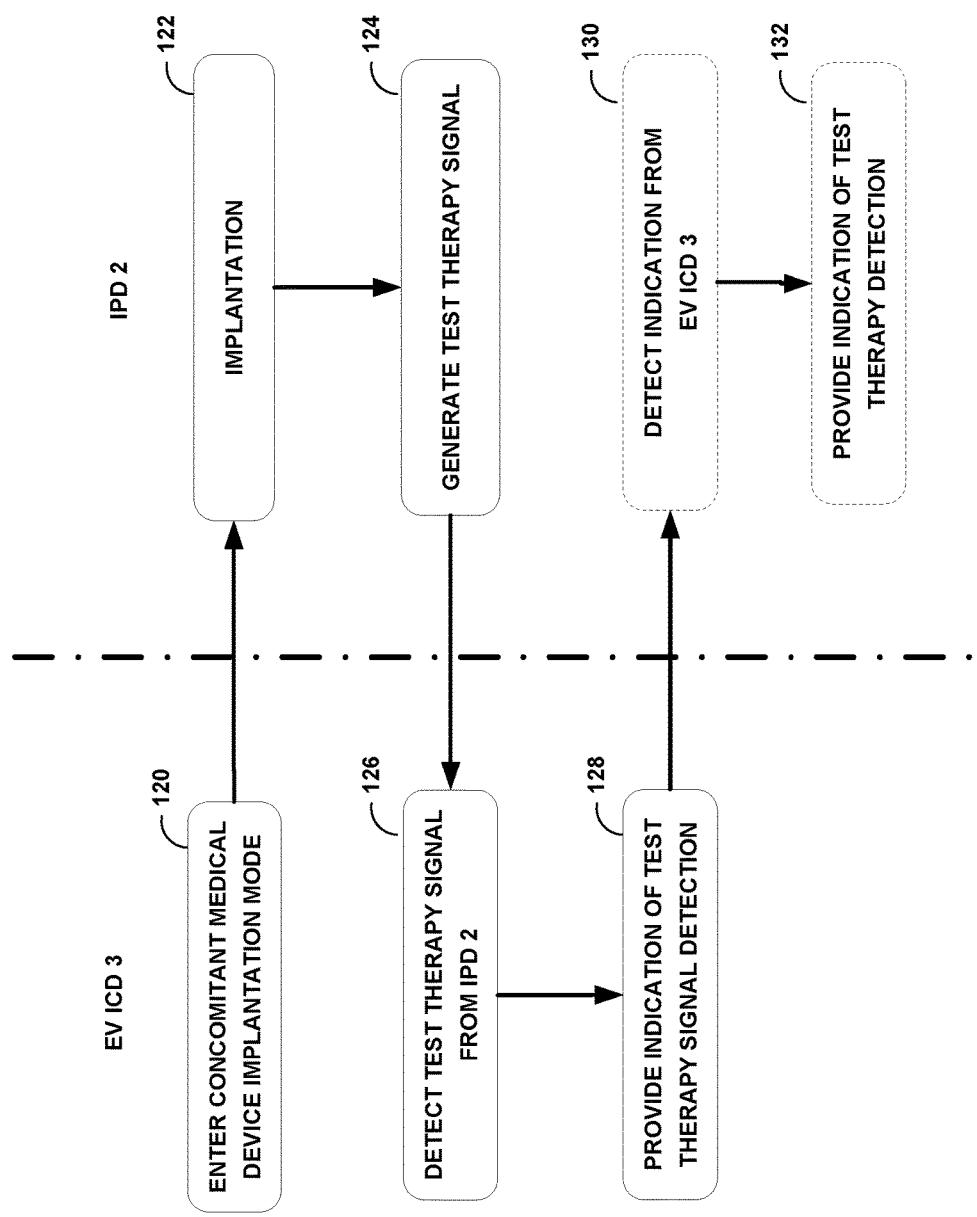
FIG. 7 is a flowchart illustrating an example operation of implantable medical devices during implantation of the later implanted medical device according to the techniques of the disclosure.

FIG. 7 is a flowchart illustrating an example operation of implantable medical devices during implantation of the later implanted medical device according to the techniques of the disclosure. For purpose of example, the example operation of FIG. 7 is described in reference to the example medical device system 10 of FIGS. 1A-1C. However, the example operation of FIG. 7 is equally applicable to the example medical device system 20 of FIGS. 2A-2C.

Prior to implanting IPD 2 within patient 12, ICD 3 receives a command to enter a concomitant medical device implantation mode (120). The clinician transmits this command to ICD 3 via telemetric commands from external device 4. While in the concomitant medical device implantation mode, ICD 3 suspends one or both of tachyarrhythmia detection and tachyarrhythmia therapy provided to patient 12. In some examples, ICD 3 suspends only a portion of tachyarrhythmia detection and/or tachyarrhythmia therapy provided to patient 12, such as one or more of tachycardia detection, fibrillation detection, ventricular defibrillation therapy, cardioversion therapy, or ATP therapy. Once ICD 3 is operating within the concomitant medical device implantation mode, the clinician implants and positions IPD 2 (122). The clinician instructs the IPD 2 to generate one or more test therapy signals (124). In some examples, the one or more test therapy signals are one or more ATP therapy pulses, bradycardia pacing therapy pulses, and/or post-shock pacing pulses.

If the clinician has positioned IPD 2 properly, ICD 3 detects the one or more test therapy signals via sensing circuitry 82 (126). Upon successful detection of the one or more test therapy signals, ICD 3 provides an indication that it has detected the one or more test therapy signals (128). In one example, upon detecting the one or more test therapy signals, processing circuitry 92 of ICD 3 instructs sound generation circuitry 90 to provide an audible notification to the clinician that ICD 3 has detected the one or more test therapy signals.

In another example, upon detecting the one or more test therapy signals, processing circuitry 92 instructs therapy delivery circuitry 84 to generate an electrical notification that is transmitted, via one or more of electrodes 9 or 11 or housing electrode 80, into patient 12. In this example, IPD 2 detects the electrical notification via sensing circuitry 56 and one or more of electrodes 34 and 40 (130). In a further example, upon detecting the one or more test therapy signals, processing circuitry 92 instructs communication circuitry 86 to transmit the electrical notification as a communication which is received by communication circuitry 56 of IPD 2.

IPD 2 transmits this electrical notification to external device 4 via communication circuitry 56, whereupon the clinician may receive the notification (132). Upon receiving the notification, the clinician may determine that IPD 2 is positioned correctly such that ICD 3 is capable of detecting when IPD 2 is administering therapy to patient 12. After transmitting the notification, ICD 3 exits the concomitant medical device implantation mode and resumes the suspended one or both of ventricular tachyarrhythmia detection and ventricular tachyarrhythmia therapy provided to patient 12. The clinician may conclude the implantation procedure, with ICD 3 and IPD 2 entering their normal modes of operation. Accordingly, ICD 3 may thereafter synchronize its therapy with the therapy provided by IPD 2 without transmitting telemetry between ICD 3 and IPD 2.

The example operation illustrated in FIG. 7 is shown for exemplary purposes only. The techniques as set forth in this disclosure may be implemented in the example operation of FIG. 7, as well as other types of operations not described specifically herein. In some configurations, ICD 3 may perform other functions prior to sending an indication that the ICD 3 has detected the one or more test therapy signals. For example, ICD 3 may ensure that it may accurately detect ventricular tachyarrhythmia in the presence of ATP therapy provided by IPD 2 prior to sending the indication. In another example, ICD 3 determines whether it may adequately communicate with IPD 2 via TCC messaging prior to sending the indication. In a further example, ICD 3 provides separate indications to respectively inform the clinician that it has detected the one or more test therapy signals, that it may accurately detect ventricular tachyarrhythmia in the presence of ATP therapy provided by IPD 2, and that it may adequately communicate with IPD 2 via TCC messaging. Nothing in this disclosure should be construed so as to limit the techniques of this disclosure to the example operation illustrated by FIG. 7.

Figure 8:
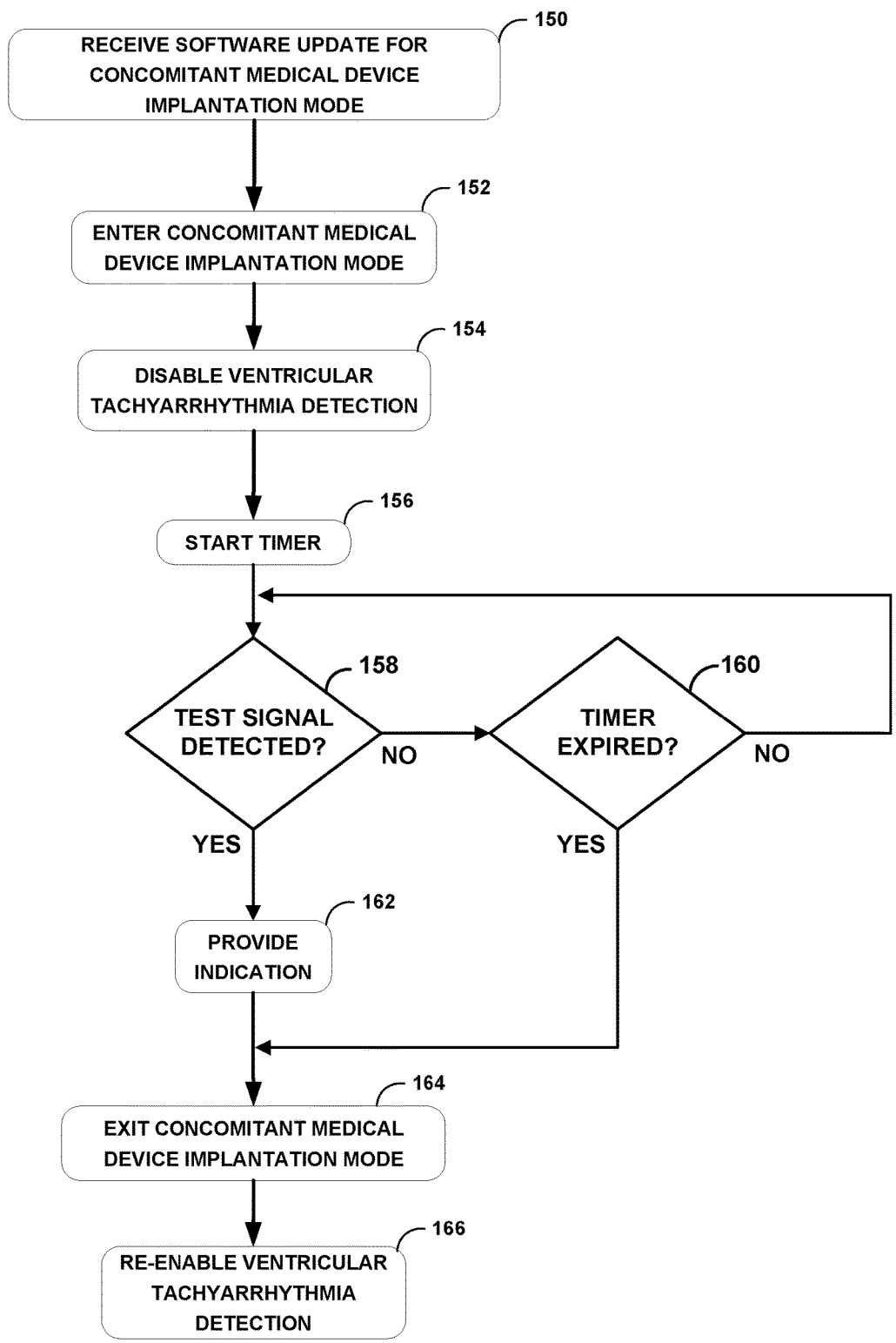
FIG. 8 is a flowchart illustrating an example operation of an extracardiovascular ICD during implantation of another medical device according to the techniques of the disclosure.

FIG. 8 is a flowchart illustrating an example operation of an extracardiovascular ICD during implantation of another medical device according to the techniques of the disclosure. For purpose of example, the example operation of FIG. 8 is described in reference to the example medical device system 10 of FIGS. 1A-1C. However, the example operation of FIG. 8 is equally applicable to the example medical device system 20 of FIGS. 2A-2C.

Prior to implanting IPD 2 within patient 12, ICD 3 receives a command from external device 4 to enter a concomitant medical device implantation mode (150). In some examples, the clinician transmits this command to ICD 3 via external device 4. ICD 3 downloads a concomitant medical device implantation mode software update 94 from external device 4 and enters the concomitant medical device implantation mode (152). While in the concomitant medical device implantation mode, ICD 3 disables therapy provided to patient 12. In the example of FIG. 8, ICD 3 disables ventricular tachyarrhythmia detection (154). However, in other examples, ICD 3 continues ventricular tachyarrhythmia detection but disables ventricular tachyarrhythmia therapy while keeping ventricular tachyarrhythmia detection enabled. After disabling therapy, ICD 3 initializes and begins a countdown timer 156.

Once ICD 3 is operating within the concomitant medical device implantation mode, the clinician implants and positions IPD 2. The clinician instructs the IPD to generate one or more test therapy signals. In some examples, the one or more test therapy signals are one or more ATP therapy pulses, bradycardia pacing therapy pulses, and/or post-shock pacing pulses.

While operating in concomitant medical device implantation mode, sensing circuitry 82 of ICD 3 continuously monitors patient 12 to determine whether it detects one or more test therapy signals from IPD 2 while decrementing the countdown timer (158). For example, sensing circuitry 82 detects cardiac signals via one or more electrodes 9a, 9b, and 11. In some examples, sensing circuitry 82 performs amplification of these signals. Sensing circuitry 82 compares the processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 92.

Processing circuitry 92 determines whether the signals identified by sensing circuitry 82 are cardiac events requiring ventricular tachyarrhythmia therapy, or are pacing signals, such as ATP therapy, provided by IPD 2. In some examples, processing circuitry 92 examines the frequency of the signal to determine whether it is a pacing pulse or a cardiac signal. In other words, if a pacing signal is delivered by IPD 2 and is of an amplitude that triggers a sensed event by sensing circuitry 82, processing circuitry 92 may reject the event as a cardiac signal because it has the signature of ATP therapy. Therefore, processing circuitry 92 would not include the event within ventricular tachyarrhythmia detection. In further examples, sensing circuitry 82 includes one or more filters to discard events having frequencies commonly associated with ATP therapy such that the events do not affect the threshold or response of the sense amplifier of sensing circuitry 82. Accordingly, processing circuitry 92 operates to ensure that ICD 3 reliable ventricular tachyarrhythmia detection and therapy in the presence of ATP therapy provided by IPD 2.

Upon detecting the one or more test therapy signals from IPD 2, ICD 3 provides an indication that ICD 3 has detected the one or more test therapy signals (162). In one example, processing circuitry 92 of ICD 3 instructs sound generation circuitry 90 to provide an audible notification to the clinician that ICD 3 has detected the one or more test therapy signals. In another example, upon detecting the one or more test therapy signals, processing circuitry 92 instructs therapy delivery circuitry 84 to generate an electrical notification that is transmitted, via one or more of electrodes 9 or 11, into patient 12, whereby IPD 2 may detect the indication.

In some examples in which ICD 3 keeps tachyarrhythmia detection enabled during the concomitant medical device implantation mode, ICD 3 may determine whether the one or more test therapy signals are inappropriately detected as one or more tachyarrhythmia events. Techniques for determining whether the test therapy signals are inappropriately detected as one or more tachyarrhythmia events are described in more detail in U.S. Patent App. Pub. No. 2015/0305640 to Reinke et al., published on Oct. 29, 2015 and entitled, "IMPLANTABLE MEDICAL DEVICE (IMD) SENSING MODIFICATIONS RESPONSIVE TO DETECTED PACING PULSES"; U.S. Patent App. Pub. No. 2015/0305641 to Stadler et al., published on Oct. 29, 2015 and entitled, "IMPLANTABLE CARDIOVERTER-DEFIBRILLATOR (ICD) TACHYARRHYTHMIA DETECTION MODIFICATIONS RESPONSIVE TO DETECTED PACING"; and U.S. Patent App. Pub. No. 2015/0305642 to Reinke et al., published on Oct. 29, 2015 and entitled, "PACE PULSE DETECTOR FOR AN IMPLANTABLE MEDICAL DEVICE," each of which is incorporated by reference herein in its entirety. If ICD 3 determines that the one or more test therapy signals are inappropriately detected as one or more tachyarrhythmia events, ICD 3 may provide an indication of the inappropriate tachyarrhythmia detection to the clinician. The indication may be audible, but may be distinct from the indication of successful detection of the therapy signal. In response to this indication, the clinician may reposition IPD 2, or change one or more parameters of the therapy signal delivered by IPD 2, or of tachyarrhythmia detection by ICD 3, to avoid the inappropriate tachyarrhythmia detection.

After providing the indication, ICD 3 exits the concomitant medical device implantation mode (164). In one example, ICD 3 automatically exits the concomitant medical device implantation mode upon generating the notification that it has detected the one or more test therapy pulses. In another example, ICD 3 receives an instruction from the clinician, via external device 4, to exit the concomitant medical device implantation mode after the clinician receives the notification. In some examples, upon exiting the concomitant medical device implantation mode, ICD 3 uninstalls the software update including the concomitant medical device implantation mode. In other words, ICD 3 removes the concomitant medical device implantation mode software update. ICD 3 resumes therapy provided to patient 12 (166). In the example of FIG. 8, ICD 3 resumes ventricular tachyarrhythmia detection. However, in other examples, ICD 3 may resume the operations that ICD 3 suspended upon entering the concomitant medical device implantation mode.

While operating in concomitant medical device implantation mode, if ICD 3 does not detect the one or more test therapy signals, ICD 3 determines whether the countdown timer has expired (160). If the timer has expired, ICD 3 exits concomitant medical device implantation mode (164) and resumes tachyarrhythmia detection and therapy provided to the patient (166) as described above.

Accordingly, the techniques of the disclosure allow a clinician to determine, during implantation, that IPD 2 is positioned correctly within the heart such that ICD 3 may detect therapy delivered to the patient by the IPD 2, without referring to the programming software or device associated with ICD 3. In some examples, the ICD 3 notifies the clinician by providing an audible sound to indicate that ICD 3 is capable of detecting the IPD therapy such that the clinician does not need to refer to the programmer software or device associated with the ICD 3, and without requiring telemetry communication between IPD 2 and ICD 3. In other examples, the ICD 3 indicates that the ICD 3 is capable of detecting the IPD therapy by providing an electrical notification to the IPD 2 via TCC messaging, such that the clinician may receive this indication via the external device 4 while executing programming software associated with IPD 2. Thus, the techniques of the disclosure may reduce the number of devices or software interfaces that the clinician must consult during the implantation procedure to determine that the IPD 2 has been positioned correctly, and that ICD 3 is appropriately detecting the therapy signal delivered by IPD 2.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. An extracardiovascular implantable cardioverter defibrillator (ICD) configured for implantation in a patient, the extracardiovascular ICD comprising:
   communication circuitry configured to receive, from an external device, a telemetric command to enter a concomitant medical device implantation mode;
   sensing circuitry configured to receive, via a plurality of electrodes, one or more test therapy signals generated by an intracardiac pacing device (IPD) implanted in the patient; and
   processing circuitry, wherein at least one of the sensing circuitry or the processing circuitry is configured to detect the one or more test therapy signals, the processing circuitry further configured to:
      cause the extracardiovascular ICD to enter the concomitant medical device implantation mode in response to receiving the telemetric command;
      cause the extracardiovascular ICD to disable at least one of ventricular tachyarrhythmia detection or ventricular tachyarrhythmia therapy in response to the extracardiovascular ICD entering the concomitant medical device implantation mode;
      detect the one or more test therapy signals while the extracardiovascular ICD is in the concomitant medical device implantation mode;
      in response to detection of the one or more test therapy signals while the extracardiovascular ICD is in the concomitant medical device implantation mode, control the extracardiovascular ICD to provide an indication that the extracardiovascular ICD has detected the one or more test therapy signals;
      cause the extracardiovascular ICD to exit the concomitant medical device implantation mode; and
      in response to the extracardiovascular ICD exiting the concomitant medical device implantation mode, cause the extracardiovascular ICD to re-enable at least one of ventricular tachyarrhythmia detection or ventricular tachyarrhythmia therapy.

2. The extracardiovascular ICD of claim 1, wherein the one or more test therapy signals comprise a first set of one or more test therapy signals, and
   wherein the processing circuitry is further configured to initiate a timer in response to the extracardiovascular ICD entering the concomitant medical device implantation mode, and
   wherein, to cause the extracardiovascular ICD to exit the concomitant medical device implantation mode, the processing circuitry is further configured to cause the extracardiovascular ICD to exit the concomitant medical device implantation mode in response to one of expiration of the timer without the sensing circuitry detecting a second set of one or more test therapy signals or the processing circuitry providing an indication that the extracardiovascular ICD has detected the second set one or more test therapy signals.

3. The extracardiovascular ICD of claim 1, wherein the processing circuitry is further configured to:
   control at least one of the sensing circuitry to detect, via the plurality of electrodes, ventricular tachyarrhythmia or therapy delivery circuitry of the extracardiovascular ICD to deliver ventricular tachyarrhythmia therapy;
   install a software update in response to receiving the telemetric command, wherein the software update comprises instructions for the concomitant medical device implantation mode including instructions that cause the extracardiovascular ICD to disable the at least one of the ventricular tachyarrhythmia detection or the ventricular tachyarrhythmia therapy in response to entering the concomitant medical device implantation mode; and
   remove the software update after providing the indication that the extracardiovascular ICD has detected the one or more test therapy signals.

4. The extracardiovascular ICD of claim 1, further comprising sound generation circuitry, wherein the processing circuitry configured to control the extracardiovascular ICD to provide the indication that the extracardiovascular ICD has detected the one or more test therapy signals is further configured to control the sound generation circuitry to provide an audible indication to a clinician.

5. The extracardiovascular ICD of claim 1, wherein the processing circuitry configured to control the extracardiovascular ICD to provide the indication that the extracardiovascular ICD has detected the one or more test therapy signals is further configured to control the communication circuitry to provide the indication to the IPD.

6. The extracardiovascular ICD of claim 1, further comprising at least one lead including at least one of the plurality of electrodes, the at least one lead configured to be implanted in subcutaneous tissue of the patient.

7. The extracardiovascular ICD of claim 1, further comprising at least one lead including at least one of the plurality of electrodes, the at least one lead configured to be implanted in a subcutaneous tissue and a sub-sternal tissue of the patient.

8. The extracardiovascular ICD of claim 1, wherein the processing circuitry configured to control the extracardiovascular ICD to provide the indication that the extracardiovascular ICD has detected the one or more test therapy signals is further configured to control the extracardiovascular ICD to provide a telemetric indication to the external device.

9. A non-transitory computer readable medium comprising instructions for causing at least one programmable processor of an extracardiovascular ICD configured for implantation in a patient to:
cause the extracardiovascular ICD to enter a concomitant medical device implantation mode in response to receiving a telemetric command to enter the concomitant medical device implantation mode;
cause the extracardiovascular ICD to disable at least one of ventricular tachyarrhythmia detection or ventricular tachyarrhythmia therapy in response to the extracardiovascular ICD entering the concomitant medical device implantation mode;
detect one or more test therapy signals generated by an intracardiac pacing device (IPD) implanted in the patient while the extracardiovascular ICD is in the concomitant medical device implantation mode; and
in response to detection of the one or more test therapy signals while the extracardiovascular ICD is in the concomitant medical device implantation mode, control the extracardiovascular ICD to provide an indication that the extracardiovascular ICD has detected the one or more test therapy signals;
cause the extracardiovascular ICD to exit the concomitant medical device implantation mode; and
in response to the extracardiovascular ICD exiting the concomitant medical device implantation mode, cause the extracardiovascular ICD to re-enable at least one of ventricular tachyarrhythmia detection or ventricular tachyarrhythmia therapy.

10. A system comprising:
a first implantable medical device comprising therapy delivery circuitry and a first plurality of electrodes, wherein the first medical device is configured to deliver one or more test therapy signals via the therapy delivery circuitry and the first plurality of electrodes; and
a second implantable medical device comprising an extracardiovascular implantable cardioverter defibrillator (ICD), the extracardiovascular ICD comprising:
communication circuitry configured to receive, from an external device, a telemetric command to enter a concomitant medical device implantation mode;
sensing circuitry configured to receive, via a second plurality of electrodes, the one or more test therapy signals; and
processing circuitry, wherein at least one of the sensing circuitry or the processing circuitry is configured to detect the one or more test therapy signals, the processing circuitry further configured to:
cause the extracardiovascular ICD to enter the concomitant medical device implantation mode in response to receiving the telemetric command;
cause the extracardiovascular ICD to disable at least one of ventricular tachyarrhythmia detection or ventricular tachyarrhythmia therapy in response to the extracardiovascular ICD entering the concomitant medical device implantation mode;
detect the one or more test therapy signals while the extracardiovascular ICD is in the concomitant medical device implantation mode;
in response to detection of the one or more test therapy signals while the extracardiovascular ICD is in the concomitant medical device implantation mode, control the second implantable medical device to provide a first indication that the second implantable medical device has detected the one or more test therapy signals;
cause the extracardiovascular ICD to exit the concomitant medical device implantation mode; and
in response to the extracardiovascular ICD exiting the concomitant medical device implantation mode, cause the extracardiovascular ICD to re-enable at least one of ventricular tachyarrhythmia detection or ventricular tachyarrhythmia therapy.

11. The system of claim 10,
wherein the processing circuitry of the second implantable medical device configured to control the second implantable medical device to provide the first indication that the second implantable medical device has detected the one or more test therapy signals is further configured to control the second implantable medical device to provide the first indication to the first implantable medical device, and
wherein the first implantable medical device is further configured to:
receive, via communication circuitry of the first implantable medical device, the first indication that the second implantable medical device has detected the one or more test therapy signals; and
provide, via the communication circuitry of the first implantable medical device, a second indication that the second implantable medical device has detected the one or more test therapy signals in response to detecting the first indication.

12. The system of claim 10, wherein the first implantable medical device is a pacing device, and the one or more test therapy signals comprises at least one cardiac pacing pulse.

13. The system of claim 12, wherein the at least one cardiac pacing pulse comprises a plurality of anti-tachycardia pacing (ATP) therapy pulses.

14. The system of claim 12, wherein the pacing device is an intracardiac pacing device comprising a housing configured for implantation within a heart of the patient.

15. An extracardiovascular implantable cardioverter defibrillator (ICD) configured for implantation in a patient, the extracardiovascular ICD comprising:
communication circuitry;
sound generation circuitry;
therapy delivery circuitry configured to deliver ventricular tachyarrhythmia therapy;
sensing circuitry configured to receive, via a plurality of electrodes, one or more test therapy signals generated by an intracardiac pacing device (IPD) implanted in the patient, wherein the sensing circuitry is further configured to detect, via the plurality of electrodes, ventricular tachyarrhythmia; and
processing circuitry, wherein at least one of the sensing circuitry or the processing circuitry is configured to detect the one or more test therapy signals, the processing circuitry further configured to receive, via the communication circuitry, a telemetric command to enter a concomitant medical device implantation mode via the communication circuitry, and, in response to receiving the telemetric command:
enter the concomitant medical device implantation mode; and
initiate a timer, wherein, while in the concomitant medical device implantation mode, the processing circuitry is configured to:
disable at least one of the ventricular tachyarrhythmia detection or the ventricular tachyarrhythmia therapy;
detect the one or more test therapy signals while the extracardiovascular ICD is in the concomitant medical device implantation mode;
in response to the detection of the one or more test therapy signals while the extracardiovascular ICD is in the concomitant medical device implantation mode, control the sound generation circuitry to provide an audible indication that the extracardiovascular ICD has detected the one or more test therapy signals; and
exit the concomitant medical device implantation mode and re-enable the at least one of the ventricular tachyarrhythmia detection or the ventricular tachyarrhythmia therapy in response to one of expiration of the timer without the detection of the one or more test therapy signals or providing the audible indication.

16. A method comprising:
receiving, by an extracardiovascular implantable cardioverter defibrillator (ICD) implanted in a patient and from an external device, a telemetric command to enter a concomitant medical device implantation mode;
entering, by the extracardiovascular ICD, the concomitant medical device implantation mode in response to receiving the telemetric command;
disabling, by the extracardiovascular ICD, at least one of ventricular tachyarrhythmia detection or ventricular tachyarrhythmia therapy in response to the extracardiovascular ICD entering the concomitant medical device implantation mode;
detecting, by the extracardiovascular ICD, one or more test therapy signals generated by another medical device implanted in the patient while the extracardiovascular ICD is in the concomitant medical device implantation mode; and
in response to detecting the one or more test therapy signals while the extracardiovascular ICD is in the concomitant medical device implantation mode, providing, by the extracardiovascular ICD, an indication that the extracardiovascular ICD has detected the one or more test therapy signals;
exiting, by the extracardiovascular ICD, the concomitant medical device implantation mode; and
in response to exiting the concomitant medical device implantation mode, re-enabling, by the extracardiovascular ICD, the at least one of ventricular tachyarrhythmia detection or ventricular tachyarrhythmia therapy.

17. The method of claim 16, wherein the one or more test therapy signals comprise a first set of one or more test therapy signals,
the method further comprising initiating, by the extracardiovascular ICD, a timer in response to entering the concomitant medical device implantation mode,
wherein exiting, by the extracardiovascular ICD, the concomitant medical device implantation mode comprises exiting the concomitant medical device implantation mode in response to one of expiration of the timer without detecting a second set of one or more test therapy signals or providing an indication that the extracardiovascular ICD has detected the second set one or more test therapy signals.

18. The method of claim 16, further comprising:
installing, by the extracardiovascular ICD, a software update in response to receiving the telemetric command, wherein the software update comprises instructions for the concomitant medical device implantation mode including instructions that cause the extracardiovascular ICD to disable the at least one of the ventricular tachyarrhythmia detection or the ventricular tachyarrhythmia therapy in response to entering the concomitant medical device implantation mode; and
removing, by the extracardiovascular ICD, the software update after providing the indication that the extracardiovascular ICD has detected the one or more test therapy signals.

19. The method of claim 16, wherein providing the indication that the extracardiovascular ICD has detected the one or more test therapy signals comprises providing a non-telemetric indication.

20. The method of claim 19, wherein providing the non-telemetric indication comprises providing an audible indication to a clinician.

21. The method of claim 16, wherein providing the indication that the extracardiovascular ICD has detected the one or more test therapy signals delivered by the other medical device comprises providing a telemetric indication to the other medical device.

22. The method of claim 16, wherein the extracardiovascular ICD comprises a subcutaneous ICD configured to sense a cardiac signal and deliver an anti-tachyarrhythmia shock from a subcutaneous location.

23. The method of claim 16, wherein the extracardiovascular ICD comprises a sub-sternal ICD configured to sense a cardiac signal and deliver an anti-tachyarrhythmia shock from an extracardiovascular and sub-sternal location.

24. The method of claim 16, further comprising:
determining, by the extracardiovascular ICD, that the one or more test therapy signals was detected as a tachyarrhythmic event; and
providing, by the extracardiovascular ICD, an indication that the one or more test therapy signals was detected as a tachyarrhythmic event.

25. The method of claim 16, wherein the other medical device comprises a pacing device, and the one or more test therapy signals comprises at least one cardiac pacing pulse.

26. The method of claim 25, wherein the at least one cardiac pacing pulse comprises a plurality of anti-tachycardia pacing (ATP) therapy pulses.

27. The method of claim 25, wherein the pacing device comprises an intracardiac pacing device comprising a housing configured for implantation within a heart of the patient.

* * * * *